US012714385B2

(12) United States Patent
Desponds

(10) Patent No.: US 12,714,385 B2
(45) Date of Patent: Aug. 25, 2026

(54) SYSTEMS AND METHODS FOR IMAGING DEVICE CALIBRATION THROUGH ANALYTICAL CORRECTION OF CHANNELIZED HOTELLING OBSERVER METRICS

(71) Applicant: GE Precision Healthcare LLC, Waukesha, WI (US)

(72) Inventor: Lionel Desponds, Buc (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 269 days.

(21) Appl. No.: 18/658,816

(22) Filed: May 8, 2024

(65) Prior Publication Data

US 2025/0345021 A1 Nov. 13, 2025

(51) Int. Cl.

*A61B 6/00* (2024.01)
*A61B 6/46* (2024.01)
*A61B 6/58* (2024.01)

(52) U.S. Cl.

CPC .............. *A61B 6/545* (2013.01); *A61B 6/461* (2013.01); *A61B 6/542* (2013.01); *A61B 6/584* (2013.01)

(58) Field of Classification Search

CPC ....... A61B 6/542; A61B 6/461; A61B 6/5258; A61B 6/582; A61B 6/545; A61B 6/584; A61B 6/032; A61B 6/4283; A61B 6/4233; A61B 6/5264; A61B 6/5235; A61B 6/5241; A61B 6/5211; A61B 6/5294; A61B 6/583; A61B 6/54; A61B 6/52; A61B 6/5205;

(Continued)

(56) References Cited

U.S. PATENT DOCUMENTS

| | | | | |
|---|---|---|---|---|
| 11,058,392 | B2 | 7/2021 | Fetterly et al. | |
| 2005/0187462 | A1 * | 8/2005 | Koh ........................ | A61B 6/481 600/416 |

(Continued)

OTHER PUBLICATIONS

Rose, A., "The Sensitivity Performance of the Human Eye on an Absolute Scale," Journal of the Optical Society of America, vol. 38, No. 2, Feb. 1948, 13 pages.

(Continued)

*Primary Examiner* — Irakli Kiknadze
(74) *Attorney, Agent, or Firm* — McCoy Russell LLP

(57) ABSTRACT

Systems and methods are disclosed for calibrating imaging devices through analytical correction of Channelized Hotelling Observer (CHO) metrics. The disclosed method corrects both finite-sample bias and residual no-signal bias in a single correction step, enhancing the calibration of medical imaging devices. The correction is based on the median of the noncentral F cumulative distribution function applied to the uncorrected d' value. This approach provides a more accurate and reliable d' value than conventional methods, which typically address only one type of bias and rely on statistical estimation of correction factors. The disclosed method is computationally efficient, rapidly computed without processing a large number of images. This enables faster and more accurate calibration of imaging system devices, facilitating improved performance and potentially enhancing diagnostic capabilities in medical imaging applications. The method can be applied to various imaging modalities, including CT, MRI, and X-ray systems.

20 Claims, 12 Drawing Sheets

(58) Field of Classification Search

CPC ........... A61B 6/585; A61B 6/58; A61B 6/586; A61B 6/504; A61B 6/5217; A61B 6/037; A61B 6/503; A61B 6/541; A61B 6/0407; A61B 6/467; A61B 6/481; A61B 6/46; A61B 6/487; A61B 6/587; A61B 6/588; A61B 6/08; A61B 6/547; A61B 6/4435; A61B 6/4441; A61B 6/4447; A61B 6/486; A61B 6/0487; A61B 6/5288; A61B 6/465; A61B 2090/374; A61B 5/061; A61B 6/12; A61B 5/339; A61B 5/06; A61B 5/062; A61B 5/721; A61B 5/1114; A61B 6/04; A61B 5/066; A61B 5/743; A61B 5/02; A61B 34/20; A61B 5/1107; A61B 6/4429; A61B 6/463; A61B 6/469; A61B 6/548; A61B 6/589; H04N 25/63; H04N 25/40; H04N 25/671; H04N 25/618; H04N 5/32; G01T 1/2018; G01T 1/2985; G06T 5/70; G06T 7/0002; G06T 2207/10116; G06T 2207/30168; G06T 5/60; G06T 7/0012; G06T 7/80; G06T 2207/10081; G06T 2207/20081; G06T 2207/20084; G06T 2207/30068; G06T 11/005; G06T 11/006; G06T 7/10; G06T 7/20; G06T 7/38; G06T 2207/10104; G06T 2210/41; G06T 2210/52; G06T 11/001; G06T 11/008; G06T 2211/404; G09B 23/30; G09G 5/02; G09G 5/026; G09G 5/14; G09G 2340/06; G09G 2340/08; G09G 2340/125; G09G 2340/14; G09G 2380/08

USPC ........................................................... 378/62

See application file for complete search history.

(56) References Cited

U.S. PATENT DOCUMENTS

| | | | | |
|---|---|---|---|---|
| 2016/0225146 A1* | 8/2016 | Frank | ................... | G06T 7/0012 |
| 2019/0320996 A1* | 10/2019 | Fetterly | ................ | A61B 6/5211 |
| 2021/0251593 A1* | 8/2021 | Oda | ..................... | H04N 25/618 |
| 2021/0319268 A1* | 10/2021 | Cohen | .................... | G06V 10/82 |

OTHER PUBLICATIONS

Barrett, H. et al., "Model observers for assessment of image quality.," PNAS, vol. 90, No. 21, Nov. 1, 1993, 8 pages.

"Medical Imaging—The Assessment of Image Quality (International Commission on Radiation Units and Measurements//ICRU Report)," International Commission on Radiation, 1st Edition, 1995, Bethesda, MD, 92 pages.

Abbey, C. et al., "Human- and model-observer performance in ramp-spectrum noise: effects of regularization and object variability," Journal of the Optical Society of America, vol. 18, No. 3, Mar. 2001, 16 pages.

Eckstein, M. et al., "Automated computer evaluation and optimization of image compression of x-ray coronary angiograms for signal known exactly detection tasks," Optics Express, vol. 11, No. 5, Mar. 10, 2003, 16 pages.

Gagne, R. et al., "Toward objective and quantitative evaluation of imaging systems using images of phantoms," Medical Physics, vol. 33, No. 1, Jan. 2006, 14 pages.

Reiser, B., "Confidence Intervals for the Mahalanobis Distance," Communications in Statistics—Simulation and Computation, vol. 30, No. 1, Aug. 17, 2006, 11 pages.

Sahu, A. et al., "Assessment of a fluorescence-enhanced optical imaging system using the Hotelling observer," Optics Express, vol. 14, No. 17, Aug. 21, 2006, 19 pages.

Deluca, P. et al., "The International Commission on Radiation Units and Measurements," Journal of the ICRU, vol. 8, No. 1, Apr. 1, 2008, 57 pages.

Caucci, L. et al., "Spatio-temporal Hotelling observer for signal detection from image sequences," Optics Express, vol. 17, No. 13, Jun. 22, 2009, 13 pages.

Wunderlich, A. et al., "Estimation of Channelized Hotelling Observer Performance with Known Class Means or Known Difference of Class Means," IEEE Transactions on Medical Imaging, vol. 28, No. 8, Aug. 2009, 10 pages.

Wunderlich, A. et al., "New Theoretical Results on Channelized Hotelling Observer Performance Estimation with Known Difference of Class Means," IEEE Transaction on Nuclear Science, vol. 60, No. 1, Jan. 11, 2013, 26 pages.

Yu, L. et al., "Prediction of human observer performance in a 2-alternative forced choice low-contrast detection task using channelized Hotelling observer: impact of radiation dose and reconstruction algorithms," Medical Physics, vol. 40, No. 4, Apr. 2013, 9 pages.

Brankov, J., "Evaluation of the channelized Hotelling observer with an internal-noise model in a train-test paradigm for cardiac SPECT defect detection," Physics in Medicine and Biology, vol. 58, No. 20, Sep. 19, 2013, 25 pages.

Favazza, C. et al., "Implementation of a channelized Hotelling observer model to assess image quality of x-ray angiography systemsm," Journal of Medical Imaging, vol. 2, No. 1, Jan. 2015, 13 pages.

Wunderlich, A. et al., "Exact Confidence Intervals for Channelized Hotelling Observer Performance in Image Quality Studies," IEEE Transactions on Medical Imaging, vol. 34, No. 2, Feb. 2015, 13 pages.

Verdun. F. et al., "Image quality in CT: From physical measurements to model observers," Physica Medica, vol. 31, No. 8, Dec. 2015, Available Online Oct. 12, 2015, 21 pages.

Fetterly, K. et al., "Direct estimation and correction of bias from temporally variable non-stationary noise in a channelized Hotelling model observer," Physics in Medicine & Biology, vol. 61, No. 5606, Jul. 6, 2016, 16 pages.

Garthwaite, P. et al., "Modified confidence intervals for the Mahalanobis distance," Statistics & Probability Letters, vol. 127, Aug. 2017, 7 pages.

Ba, A. et al., "Inter-laboratory comparison of channelized hotelling observer computation," Medical Physics, vol. 45, No. 7, Jul. 2018, Available Online Apr. 28, 2018, 22 pages.

Eckel, S. et al., "Establishment and validation of the Channelized Hotelling Model Observer for image assessment in industrial radiography," NDT & E International, vol. 98, Sep. 2018, 7 pages.

Fetterly, K. et al., "Performance assessment of active vs passive pixel x-ray angiography detector systems using a bias-corrected channelized Hotelling observer and adult patient-equivalent experimental conditions," Medical Physics, vol. 45, No. 11, Nov. 2018, Available Online Oct. 12, 2018, 9 pages.

Tao, A. et al., "Integration of high velocity test object motion into a channelized Hotelling observer for the assessment of x-ray angiography systems," Physics in Medicine and Biology, vol. 64, No. 18, Sep. 17, 2019, 27 pages.

Samei, E. et al., "Performance evaluation of computed tomography systems: Summary of AAPM Task Group 233," Medical Physics, vol. 46, No. 11, Nov. 2019, Available Online Sep. 11, 2019, 44 pages.

Lee, C. et al., "Human observer performance on in-plane digital breast tomosynthesis images: Effects of reconstruction filters and data acquisition angles on signal detection," PLoS One, vol. 15, No. 3, Mar. 12, 2020, 20 pages.

Vaishnav, J. et al., "CT metal artifact reduction algorithms: Toward a framework for objective performance assessment," Medical Physics, vol. 47, No. 8, Aug. 2020, 33 pages.

Gomez-Cardona, D. et al., "Task-specific efficient channel selection and bias management for Gabor function channelized Hotelling observer model for the assessment of x-ray angiography system performance," Medical Physics, vol. 48, No. 7, Jul. 2021, Available Online May 30, 2021, 40 pages.

(56) References Cited

OTHER PUBLICATIONS

Fan, M. et al., "Accurate and efficient measurement of channelized Hotelling observer-based low-contrast detectability on the ACR CT accreditation phantom," Medical Physics, vol. 50, No. 2, Feb. 2023, Available Online Nov. 12, 2022, 13 pages.

Valeri, F. et al., "UNet and MobileNet CNN-based model observers for CT protocol optimization: comparative performance evaluation by means of phantom CT images," Journal of Medical Imaging, vol. 10, Suppl. 1, Feb. 2023, Available Online Mar. 7, 2023, 19 pages.

Ingraito, C. et al., "Spatio-temporal generalized Model Observers methods for Low Contrast Detectability assessment in digital angiography: Application to moving targets," Physica Medica, vol. 108, Apr. 2023, Available Online Mar. 9, 2023, 12 pages.

Göppel, M. et al., "Dose-efficiency quantification of computed tomography systems using a model-observer," Medical Physics, vol. 50, No. 12, Dec. 2023, Available Online May 14, 2023, 12 pages.

Evans, K. et al., "Special Issue Editorial: Medical Image Perception and Observer Performance," Journal of Medical Imaging, vol. 10, No. S1, Aug. 23, 2023, 5 pages.

* cited by examiner

600
Noncentral F cumulative distribution for d' input, 96 channels, 1200 images
1
0.9
0.8
0.7
0.6
0.5
0.4
0.3
0.2
0.1
0
0.3
0.4
0.5
0.6
0.7
0.8
0.9
1
Uncorrected d' 602
Confidence interval minimum 604
Confidence interval maximum 606
F-median (confidence interval 50%) 610
d', zero-signal corrected 608

700 d' residual at zero-signal vs CI at 50% (d' residual decreases for each channel with the number of images: 100, 200, 400, 800, 1200, 20000)

First non-zero CI_50%

0
0.2
0.4
0.6
0.8
1
1.2
1.4

0 0.2 0.4 0.6 0.8 1 1.2 1.4 d' at zero signal (average on 10 samples)

3-DOG
4-BP
10-DDOG
40-Gabor
96-Gabor
Linear fit on all channels 800
2.00
1.50
1.00
0.50
0.00
0
0.002
0.004
0.006
0.008
0.01
1/Number of images
Uncorrected d' 802
Gamma corrected d' 804
F-median corrected d' 806
Linear fit to uncorrected d' 808
Linear fit to gamma corrected d' 810
Linear fit to F-median corrected d' 812

1000

SYSTEMS AND METHODS FOR IMAGING DEVICE CALIBRATION THROUGH ANALYTICAL CORRECTION OF CHANNELIZED HOTELLING OBSERVER METRICS

TECHNICAL FIELD

The present disclosure relates generally to the field of medical imaging systems and, more particularly, to calibration of imaging devices through analytical correction of biases in Channelized Hotelling Observer metrics.

BACKGROUND

In the field of medical imaging, the design and calibration of imaging devices plays an important role in enabling diagnostic accuracy and improving patient outcomes. Imaging device calibration involves the assessment of image quality, which is quantified using observer performance metrics. One such metric is the Channelized Hotelling Observer (CHO) metric, which serves as a statistical model simulating human observer visual performance for specific visual tasks. The CHO metric, denoted as d', is a scalar value recognized for its correlation with human observer responses. Due to its efficacy in mimicking human observers, the CHO metric is accepted by regulatory bodies such as the FDA as objective evidence of object detectability for improvement claims in medical device submissions.

However, recognized limitations in the use of CHO as an observability metric include biases which limit the utility of the CHO metric in imaging device calibration. Two forms of bias that affect the CHO metric are the finite-sample bias and the bias at no-signal. Finite-sample bias results from a dependence of the d' value on the number of images used to determine d', independent of the underlying signal and noise properties of the images. The finite sample bias may result in different values of d' being determined for two distinct sets of images, even when object detectability in both image sets is equivalent, due simply to the number of images in both sets being different.

Bias at no-signal occurs when the d' value does not approach zero even in the absence of a signal, indicating a residual bias. This bias can be attributed to factors including the inherent properties of the imaging detectors and the statistical computation methods employed. The presence of such biases can affect the reliability of the CHO metric, potentially leading to suboptimal device design and performance particularly in tasks such as nominal dose determination, which may involve acquisition of images at low signal-to-noise ratios, where the bias at no-signal more strongly impacts the d'.

Conventional approaches aimed at mitigating the above biases have employed methods such as gamma correction and re-sampling based linear extrapolation techniques, and in all cases seek to address only one or the other of the above biases. However, these approaches may not always yield accurate results, and/or may be computationally expensive. For example, in the re-sampling based linear extrapolation approach, d' is computed for multiple distinct image sets of various sizes (that is, comprising different numbers of images) in order to determine and correct for the sample size dependence of d' (i.e., the finite sample bias). Computing multiple estimates of d' is computationally expensive, and the extrapolated d' value may retain inaccuracies due to approximate nature of this approach. Further, no single approach successfully mitigates both the bias at no signal and the finite-sample bias. Therefore, there is a need for a precise and efficient method to correct both finite-sample bias and residual no-signal bias in the estimation of the CHO metric, thereby enhancing the calibration of medical imaging devices.

BRIEF DESCRIPTION

The present disclosure at least partially addresses the issues described above. In one embodiment, a method for calibrating an imaging system includes initializing imaging system parameters, selecting channels based on the initialized imaging system parameters, and acquiring a plurality of noise images using the imaging system parameters. The method further includes acquiring a plurality of signal images using the imaging system parameters, correcting non-uniformities present in the plurality of noise images and the plurality of signal images, and determining an uncorrected detectability index (d') for the imaging system based on the corrected plurality of noise images, the corrected plurality of signal images, and the channels. The uncorrected d' is corrected based on a median of an F-distribution of the uncorrected d' to obtain a corrected d'. The method also includes comparing the corrected d' to a predetermined threshold and adjusting the imaging system parameters based on the comparison of the corrected d' to the predetermined threshold.

In another embodiment, an imaging system is provided, comprising a memory storing instructions, an imaging device, and a processor communicably coupled to the memory and the imaging device. The processor is configured to execute the instructions to initialize imaging system parameters for the imaging device, select channels based on the initialized imaging system parameters, and acquire a plurality of noise images and a plurality of signal images using the imaging system parameters. The processor is further configured to correct non-uniformities present in the acquired plurality of noise images and the plurality of signal images, determine an uncorrected detectability index (d') for the imaging system based on the corrected plurality of noise images, the corrected plurality of signal images, and the channels, and correct the uncorrected d' based on a median of an F-distribution of the uncorrected d' to obtain a corrected d'. Additionally, the processor is configured to compare the corrected d' to a predetermined threshold and adjust the imaging system parameters based on the comparison of the corrected d' to the predetermined threshold.

In yet another embodiment, a method for calibrating parameters of an imaging system includes initializing imaging system parameters and acquiring a plurality of noise images using the initialized imaging system parameters. The method also includes acquiring a plurality of signal images using the initialized imaging system parameters, correcting image non-uniformities present in the plurality of noise images and the plurality of signal images, and selecting a plurality of channels. The method further includes channelizing the plurality of noise images and the plurality of signal images using the plurality of channels to produce a plurality of channelized noise images and a plurality of channelized signal images, determining an uncorrected detectability index (d') based on the plurality of channelized noise images and the plurality of channelized signal images, and correcting the uncorrected d' based on a median of an F-distribution of the uncorrected d' to obtain a corrected d'. The method concludes with displaying a calibration assessment report based on the corrected d'.

The disclosed approach introduces a novel method for calibrating imaging devices by addressing both the no-signal bias and the finite-sample bias in the estimation of the CHO metric. This method employs an analytical correction that simultaneously corrects for both types of bias, thereby providing a more accurate and reliable d' value. The correction is based on the median of the noncentral F cumulative distribution function, which is applied to the uncorrected d' value. This innovative approach is distinct from conventional methods, which typically address only one type of bias and often rely on statistical estimation of correction factors. By recognizing the interrelated nature of the no-signal bias and the finite-sample bias, the disclosed approach offers a more precise correction that is not subject to the inaccuracies inherent in statistical estimation.

Furthermore, the disclosed method demonstrates a significant improvement in computational efficiency over traditional approaches. Conventional methods, such as resampling based linear extrapolation, require the processing of hundreds of images to estimate correction factors, which can be both time-consuming and computationally intensive. In contrast, the disclosed method utilizes an analytical correction that can be computed rapidly, without the need to process a large number of images. This efficiency is achieved by directly applying the median of the F-distribution to the uncorrected d' value, resulting in a corrected d' that substantially mitigates the biases that affect conventional methods. Consequently, the disclosed method enables faster and more accurate calibration of imaging system devices, facilitating better performance and potentially enhancing diagnostic capabilities in medical imaging applications.

The above advantages and other advantages, and features of the present disclosure will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
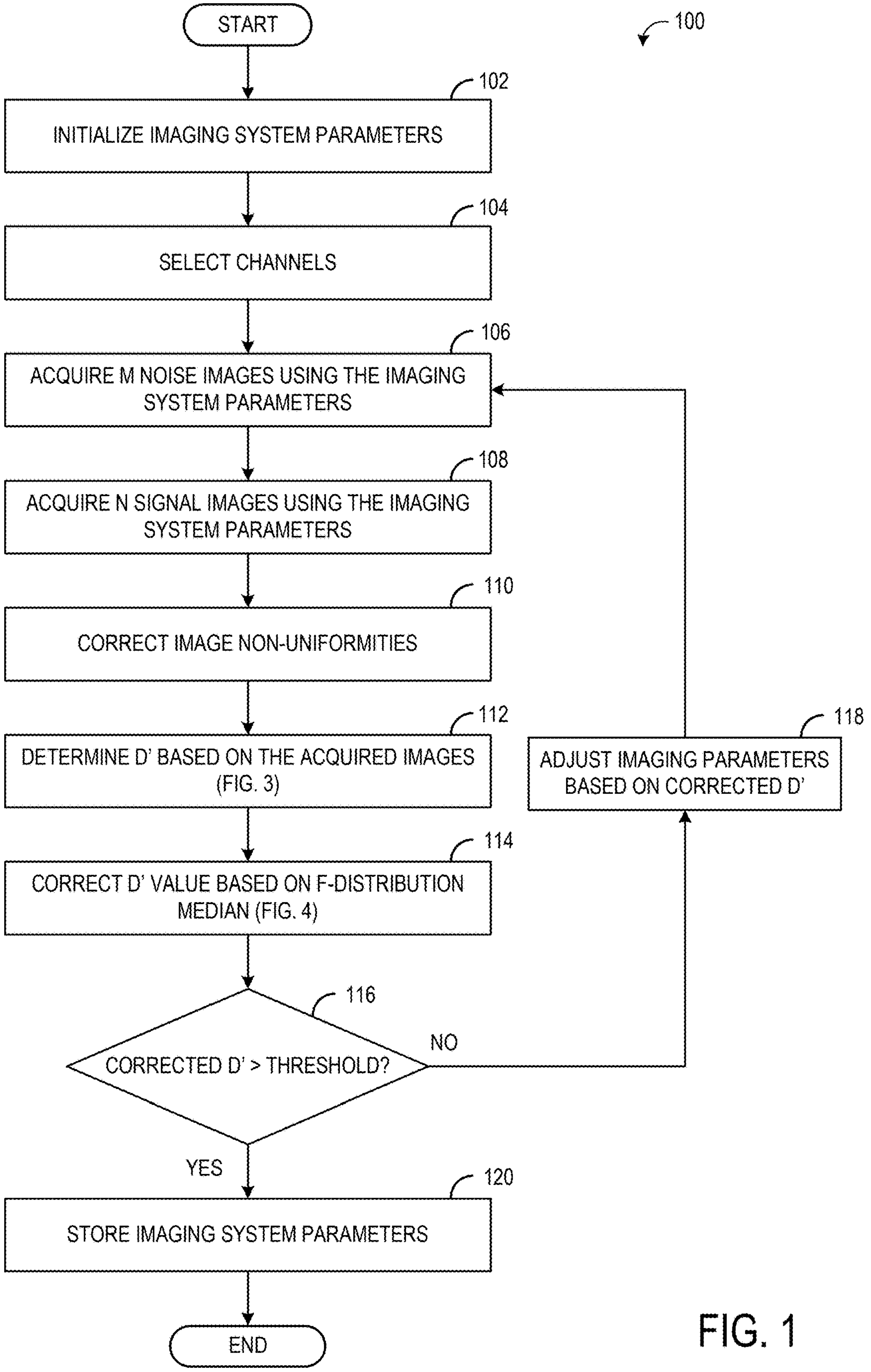
FIG. 1 is a flowchart illustrating a method for calibrating an imaging system using a corrected detectability index (d')

The drawings illustrate specific aspects of the described systems and methods for calibrating imaging devices through analytical correction of CHO metrics. Together with the following description, the drawings demonstrate and explain the principles and operation of the described systems and methods. In the drawings, the size and relative positions of components may be exaggerated for clarity, and well-known structures, materials, or operations are not shown or described in detail to avoid obscuring aspects of the systems and methods described herein.

DETAILED DESCRIPTION

The present disclosure provides systems and methods for calibrating imaging system devices through analytical correction of Channelized Hotelling Observer (CHO) metrics. The disclosed systems and methods enable precise and reliable image quality assessment in medical imaging, which may be particularly advantageous for accurate diagnostics and patient care. Conventional approaches for calibrating imaging devices have relied on the CHO metric, a statistical model simulating human observer visual performance. However, these conventional methods have been limited by biases such as finite-sample bias and bias at no-signal, which may significantly impact the reliability of the CHO metric and, consequently, the calibration of imaging devices. The disclosed systems and methods introduce a correction technique that simultaneously addresses both types of bias, providing a more accurate and computationally efficient means of calibrating imaging devices.

The disclosed method employs an analytical correction based on the median of the noncentral F cumulative distribution function, which is applied to the uncorrected d' value. This approach is distinct from prior methods that typically address only one type of bias and often rely on statistical estimation of correction factors. By recognizing the interrelated nature of the no-signal bias and the finite-sample bias, the disclosed approach offers a precise correction that is not subject to the inaccuracies inherent in statistical estimation. Furthermore, the disclosed method demonstrates an improvement in computational efficiency over traditional approaches, such as re-sampling based linear extrapolation, which require the processing of numerous images to estimate correction factors. The analytical correction can be computed rapidly, without the need to process a large number of images, resulting in a corrected d' that mitigates the biases that affect conventional methods.

The technical advantages of the disclosed systems and methods include providing an accurate d' value, enabling optimization of imaging system devices, which may lead to improved image quality and enhanced diagnostic capabilities. The analytical correction method can be applied to various imaging modalities, including Computed Tomography (CT), Magnetic Resonance (MR) imaging, and X-ray systems. Additionally, the computational efficiency of the disclosed method facilitates rapid calibration of imaging devices, which may be beneficial in clinical environments where time efficiency is particularly relevant.

Figure 3:
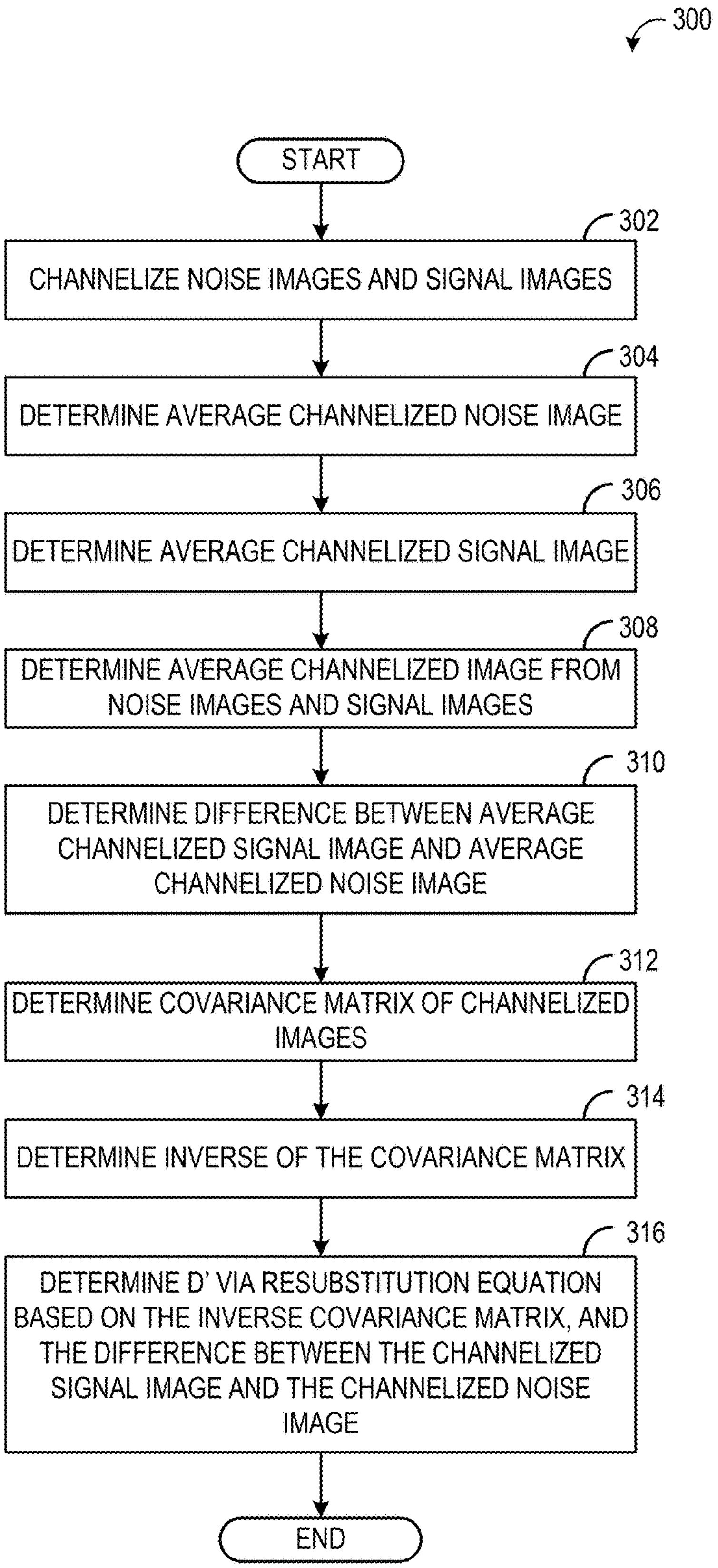
FIG. 3 is a flowchart illustrating a method for determining an uncorrected detectability index, d', via channelization of noise and signal images.
Figure 4:
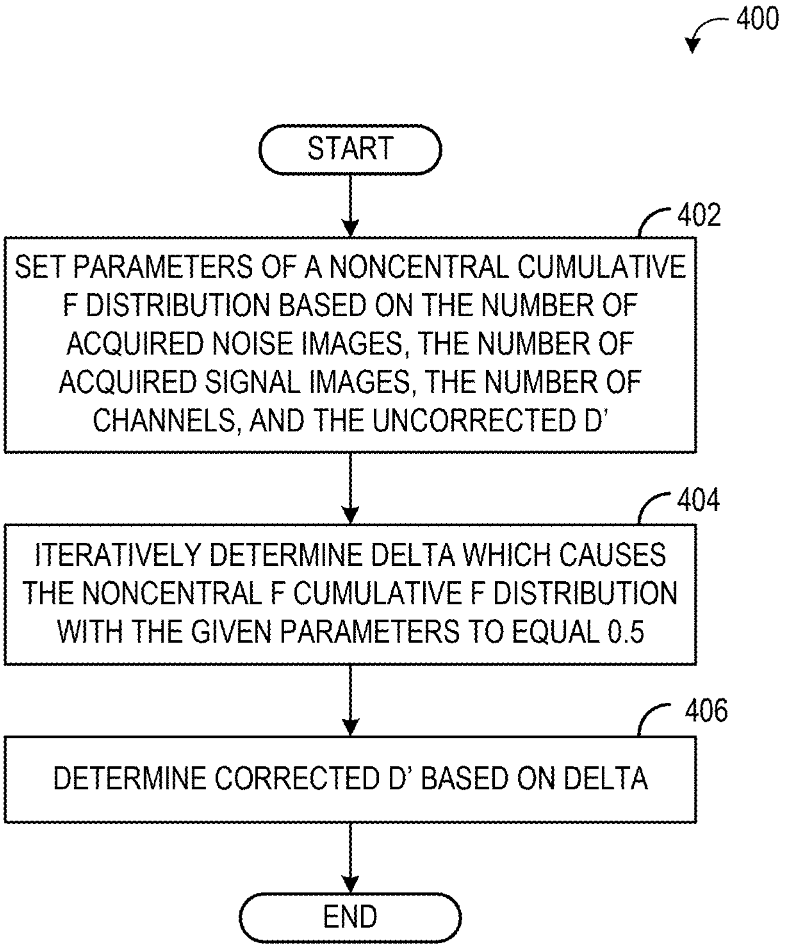
FIG. 4 is a flowchart illustrating a method for correcting the uncorrected d' value, based on a noncentral F cumulative distribution.
Figure 5:
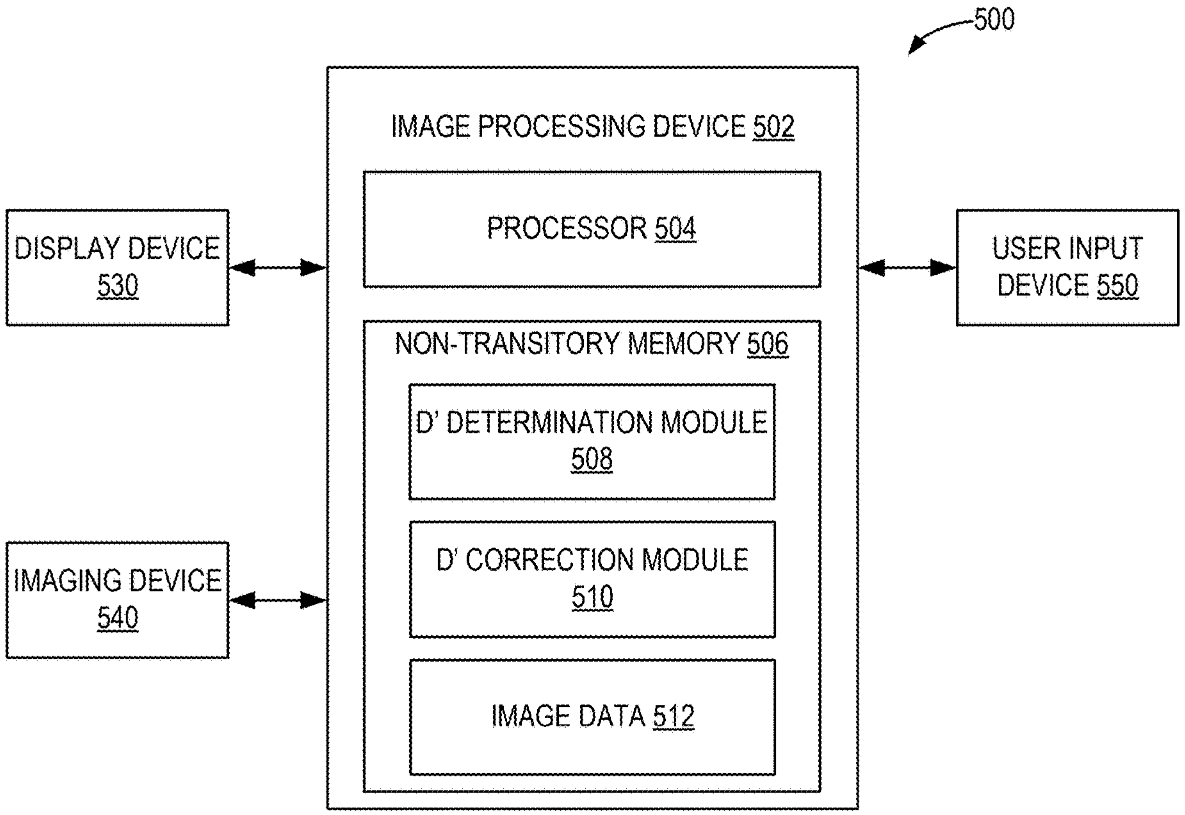
FIG. 5 is a schematic diagram of an image processing device.

In one embodiment, a method for calibrating an imaging system is disclosed, which utilizes a corrected detectability index (d') to enhance the accuracy of image quality assessments. The calibration method is depicted in FIG. 1, which presents a flowchart illustrating the steps involved in the calibration process using the corrected d'. The method further includes generating a calibration assessment report, as outlined in FIG. 2, which utilizes the corrected d' to provide an evaluation of the imaging system's performance. FIG. 3 illustrates a flowchart of a method for determining the uncorrected d' via channelization of noise and signal images. Subsequently, FIG. 4 provides a flowchart illustrating a method for correcting the uncorrected d' value. This correction is based on a noncentral F cumulative distribution, which accounts for the finite sample size effects that can bias the uncorrected d' value. An image processing device, which may be employed to perform the methods described herein, is schematically depicted in FIG. 5. This device is configured to process image data and calculate the detectability indices necessary for the calibration of the imaging system.

Figure 6:
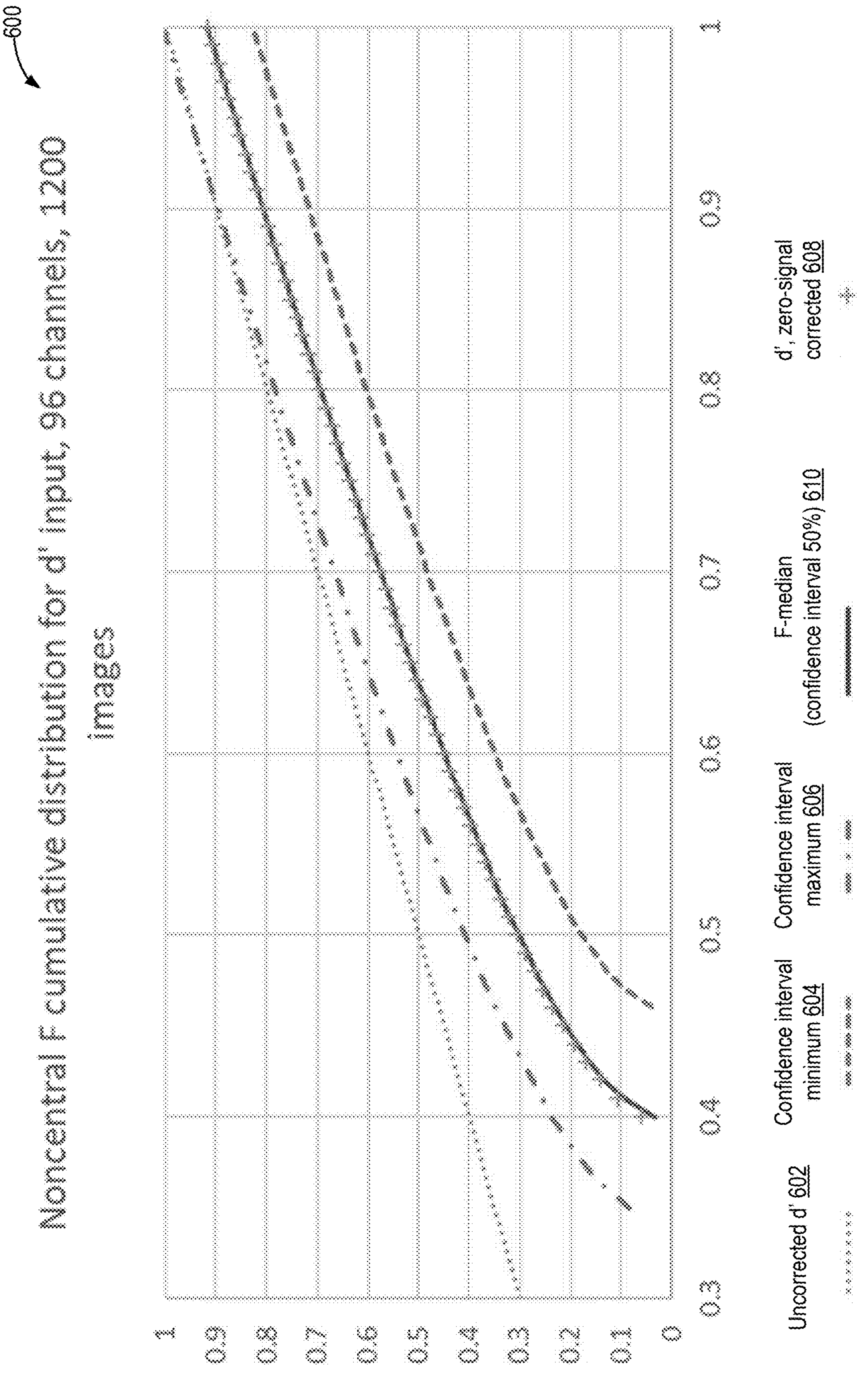
FIG. 6 is a graphical depiction of an uncorrected detectability index, d', a corrected detectability index.
Figure 7:
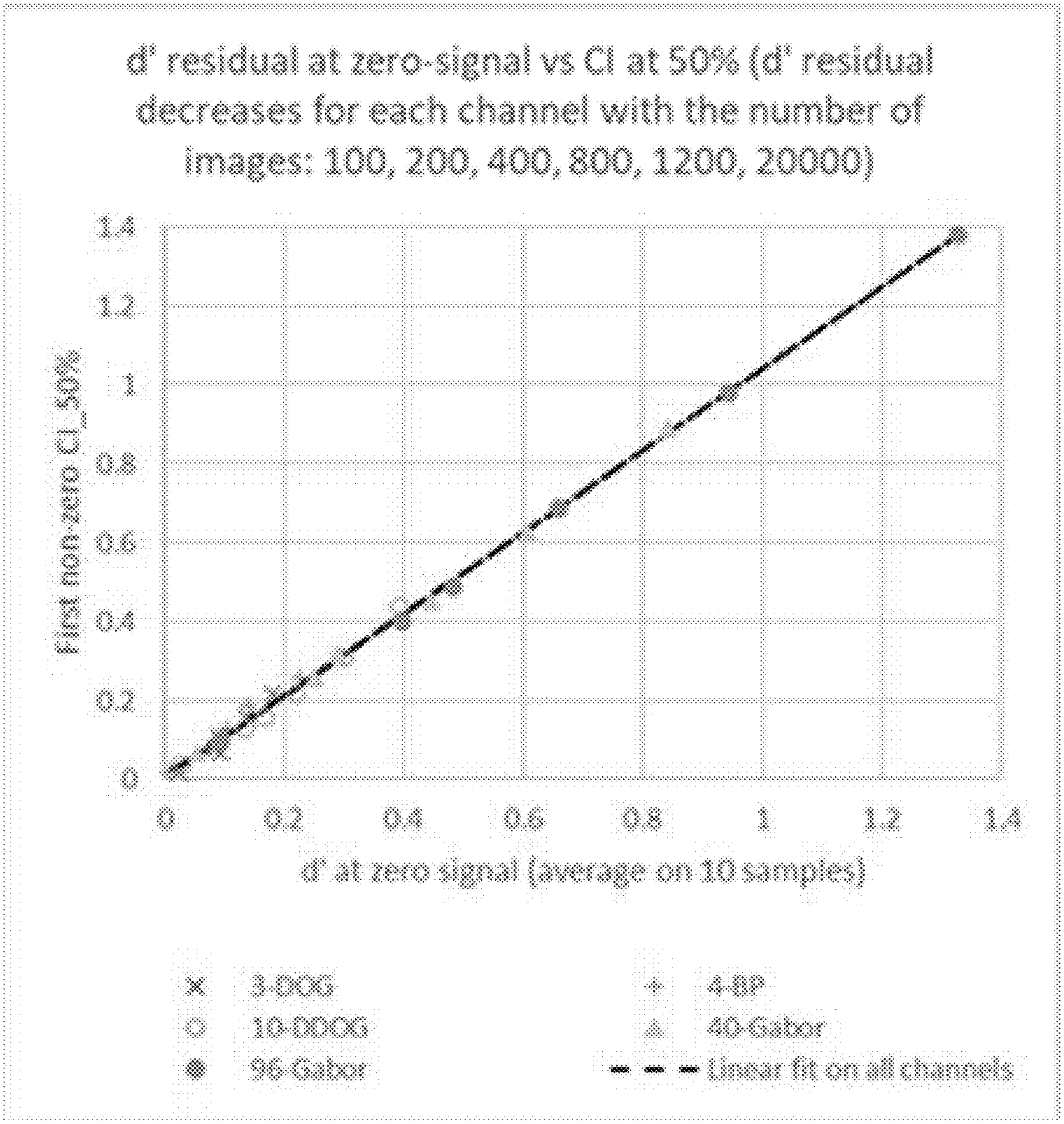
FIG. 7 is a graphical depiction of the correlation between the zero-signal residual under various conditions and the uncorrected d' input which results in a zero value using the disclosed noncentral F cumulative distribution based d' correction.
Figure 8:
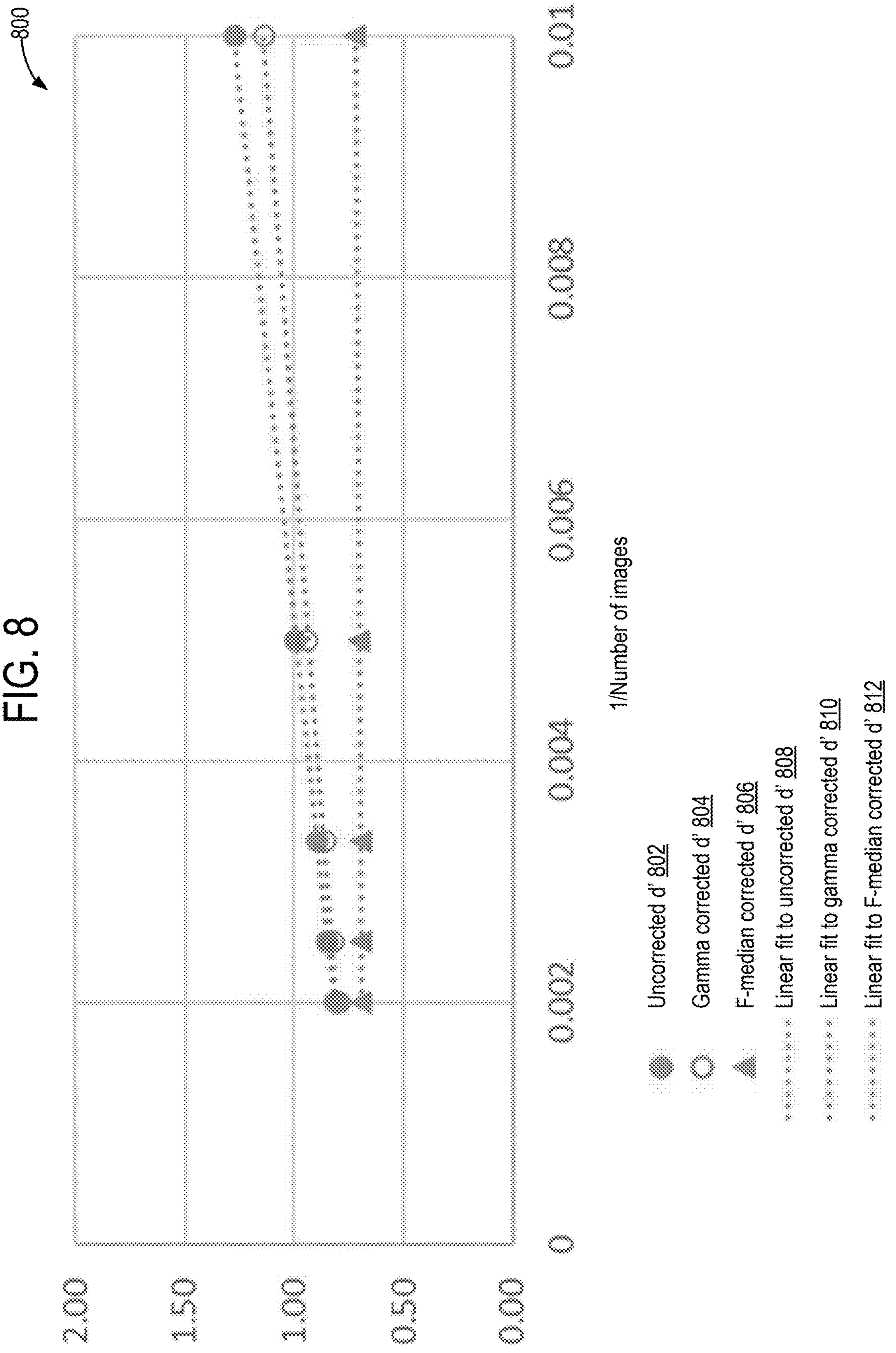
FIG. 8 shows a comparison between the finite sample bias of d' with various bias corrections, e.g., no correction, gamma correction, and noncentral F cumulative distribution based correction.
Figure 9:
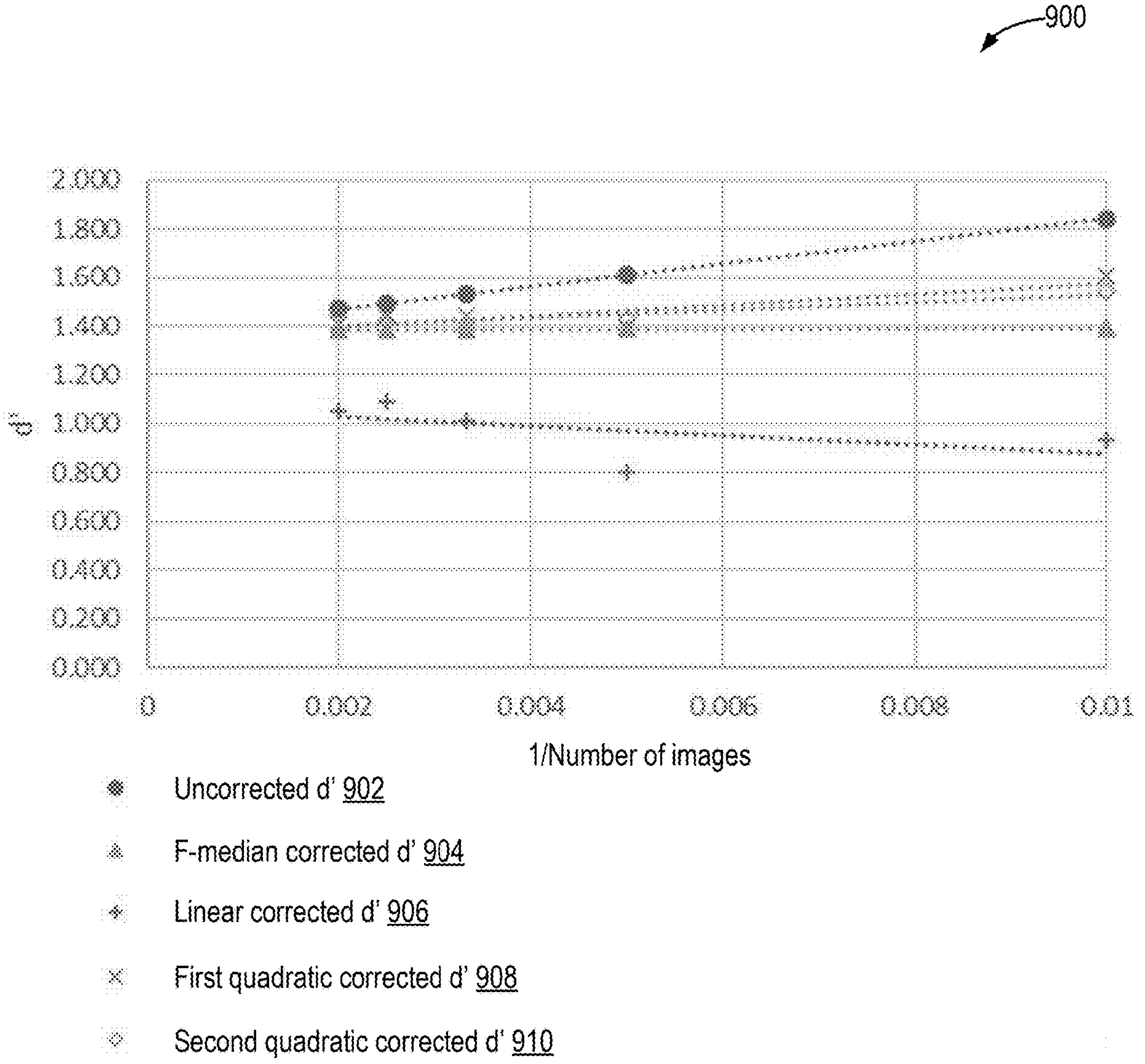
FIG. 9 shows a comparison between the finite sample bias of d' with various bias corrections.
Figure 10:
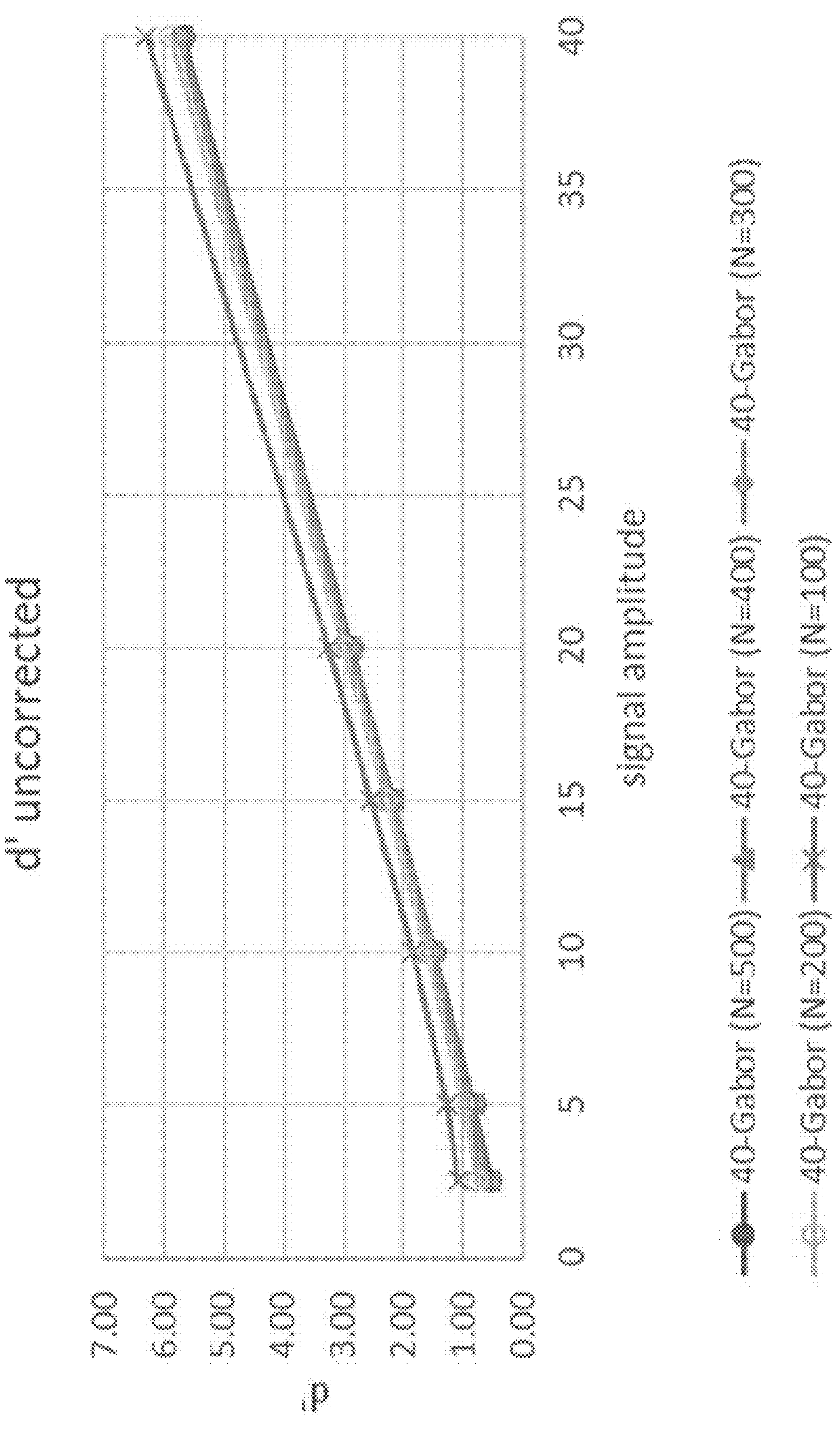
FIGS. 10, 11, and 12 show graphical comparisons of the no-signal and finite sample biases under various bias corrections.
Figure 11:
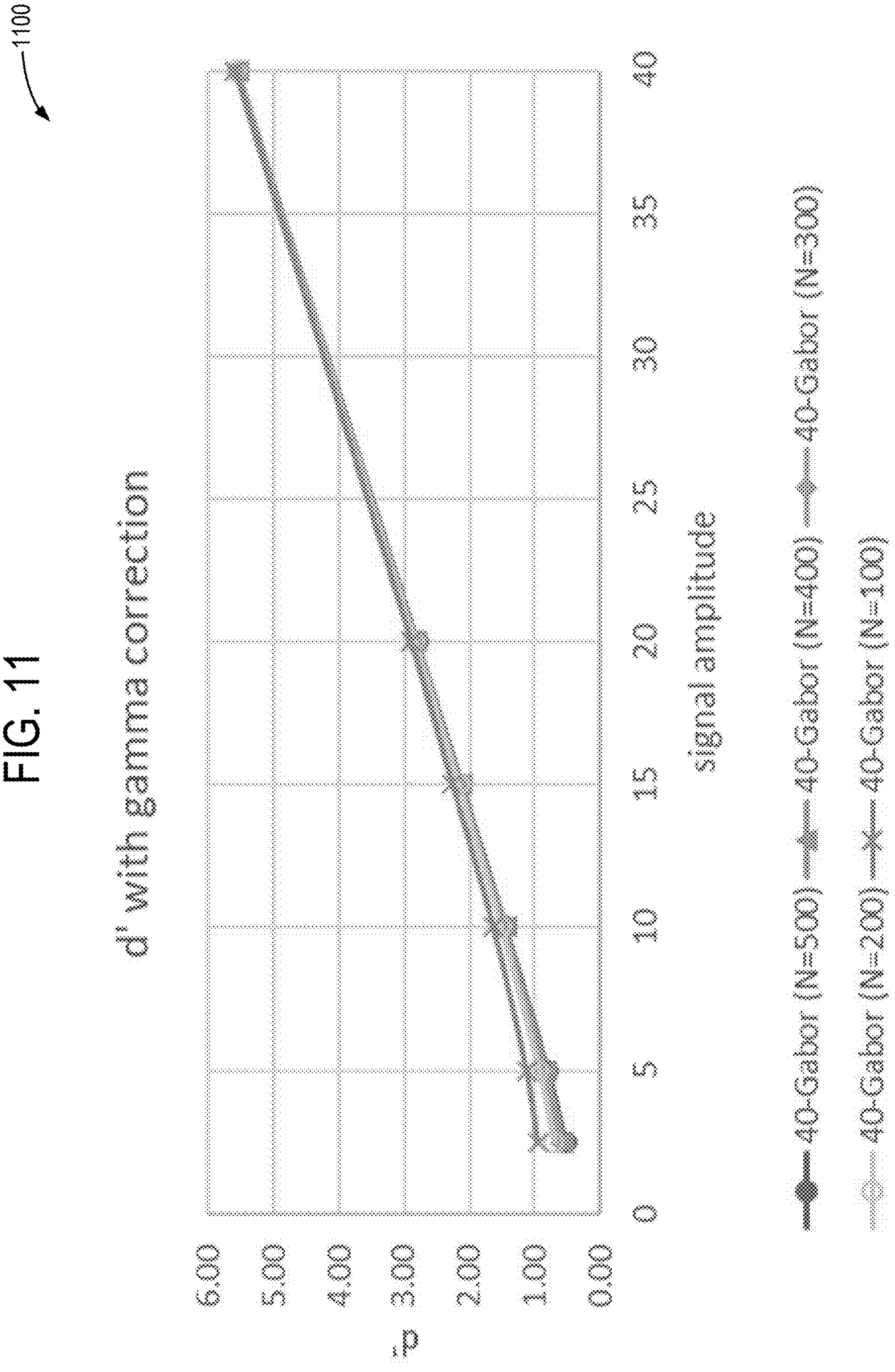
Figure 12:
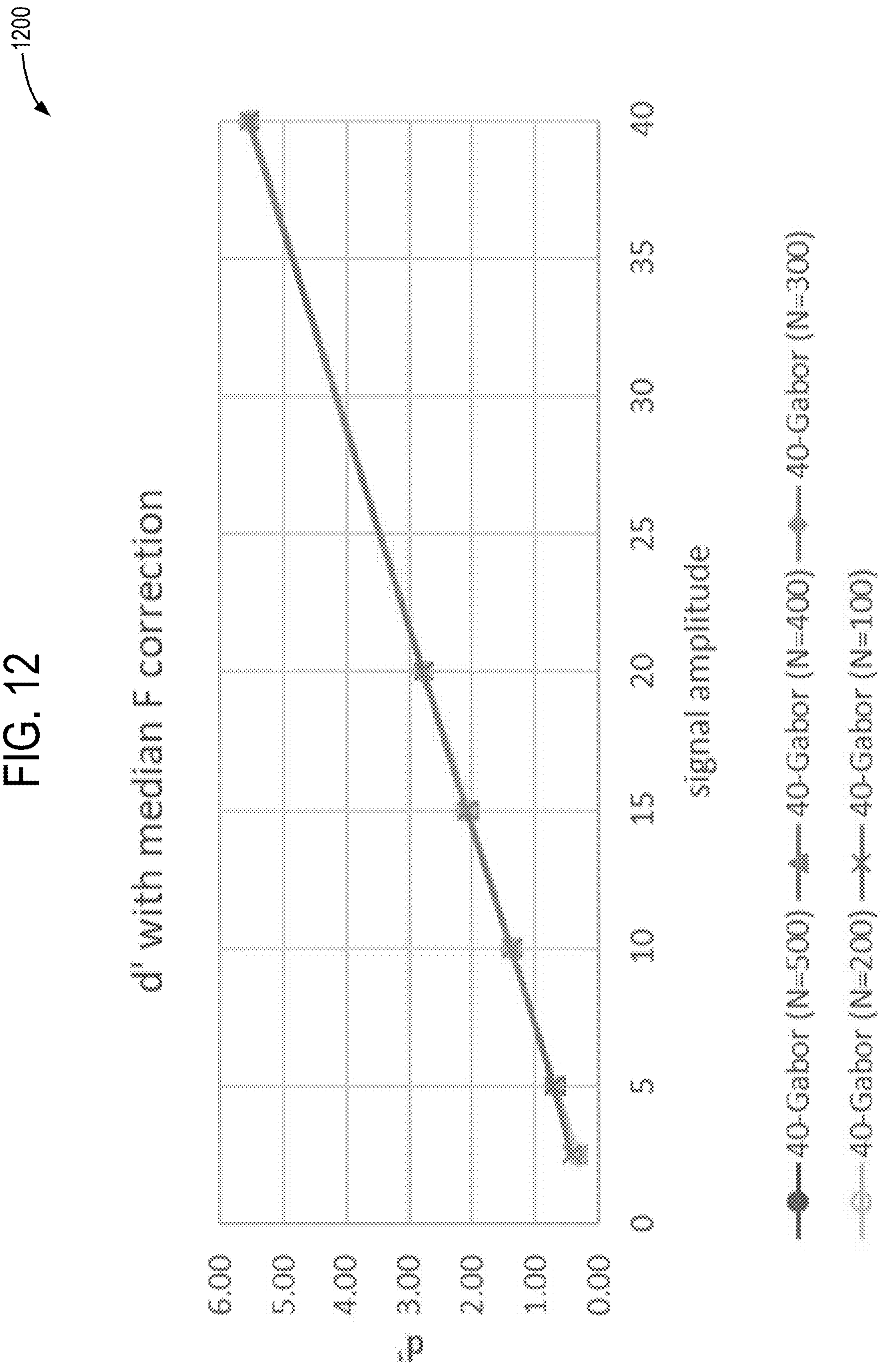

The graphical depiction of the uncorrected and corrected detectability indices is provided in FIG. 6, illustrating the impact of the correction on the d' value. FIG. 7 further illustrates the relationship between the zero-signal residual under various conditions and the uncorrected d' input, demonstrating how the disclosed noncentral F cumulative distribution based d' correction results in a zero d' at zero signal. Comparative analyses of the finite sample bias of d' with various bias corrections are shown in FIGS. 8 and 9. These figures compare the performance of different correction methods, including no correction, gamma correction, and the noncentral F cumulative distribution based correction, highlighting the advantages of the disclosed method. Finally, FIGS. 10, 11, and 12 provide graphical comparisons of the no-signal and finite sample biases under various bias corrections. These comparisons further illustrate the effectiveness of the disclosed correction method in reducing bias and improving the reliability of the detectability index as a metric for imaging system calibration.

Referring to FIG. 1, a flowchart of a method 100 for calibrating an imaging system is shown. The method 100 may be employed by an image processing system to enhance the accuracy of image quality assessments, thereby facilitating improved diagnostic capabilities in medical imaging applications.

At operation 102, the image processing system initializes imaging system parameters for the imaging device. This operation establishes the baseline settings that will be used for image acquisition. The initialization may include setting parameters such as exposure levels, voltage, current, and other imaging conditions that are used for obtaining high-quality images. In one embodiment, the system may initialize parameters specifically tailored for different imaging modalities, such as Computed Tomography (CT), Magnetic Resonance Imaging (MRI), or X-ray systems. In another embodiment, the system may initialize parameters based on a predetermined protocol for a particular diagnostic task or patient demographic.

At operation 104, the system selects channels based on the initialized imaging system parameters. Channels refer to the filters or transformations applied to the image data to facilitate the extraction of relevant features. The selection of the number and type of channels influences the performance of the CHO metric. In one embodiment, the system may select channels such as Difference of Gaussians (DOG), dense DOG (DDOG), Gabor, Bandpass, or Laguerre-Gauss filters, based on a particular imaging task to be performed. In another embodiment, the system may select channels based on a priori knowledge of the imaging system's characteristics or the specific diagnostic task at hand.

At operation 106, the system acquires a plurality of noise images using the initialized imaging system parameters. Noise images are captured without the presence of a signal, and are used to characterize the noise properties of the imaging system. The number of noise images, denoted as M, is a factor in the calibration process. In one embodiment, the system may acquire noise images at different locations within the system's field of view to ensure comprehensive noise characterization. In another embodiment, the system may acquire noise images under varying imaging conditions to account for potential variations in noise levels.

Following the acquisition of noise images, at operation 108, the system acquires a plurality of signal images using the initialized imaging system parameters. Signal images are those captured with the presence of a signal, such as a test object or a phantom, and are used to assess the system's ability to detect the signal amidst the noise. The number of signal images, denoted as N, is selected to provide a representative number of images to infer the signal properties for the current imaging system parameters. In one embodiment, the system may acquire signal images with varying signal strengths to evaluate the system's detectability performance across a range of conditions. In another embodiment, the system may acquire signal images with different signal-to-noise ratios to simulate various clinical scenarios.

At operation 110, the image processing system corrects for image non-uniformities within and between the acquired noise and signal images for the computation of the CHO metric, to produce a corrected plurality of signal images and a corrected plurality of noise images. Non-uniformities, which may arise from variations in detector sensitivity, beam hardening effects, or scatter radiation, can introduce biases into the CHO metric, affecting the calibration integrity of the imaging system. In some embodiments, the system applies a flat-field correction to homogenize average pixel intensity values across the images, mitigating the impact of detector non-uniformities and ensuring that the CHO metric accurately reflects signal detectability instead of variations in overall image signal intensity. Additionally, the system may employ correction algorithms that address both spatial and temporal variations in the image data, enhancing the accuracy and reliability of the CHO metric for device calibration. The corrections at operation 110 may lead to a more precise estimation of the d' value, enabling the development of imaging systems capable of accurately determining d' values even for particularly low signal intensity images, and ensuring consistent and repeatable measurements of image quality for calibration over time and across systems.

Operation 112 involves determining an uncorrected detectability index (d') for the imaging system based on the corrected plurality of noise images and the corrected plurality of signal images. The uncorrected d' quantifies the system's ability to distinguish between noise and signal. In one embodiment, the system may compute d' using the resubstitution method, which involves training and testing the CHO on the same set of images. The determination of the uncorrected d' will be discussed in more detail below with reference to method 300 shown in FIG. 3.

At operation 114, the system corrects the uncorrected d' value based on the median of an F-distribution. In one embodiment, the system may determine the noncentrality parameter (δ, also referred to herein as delta) of a noncentral F cumulative distribution (ncfcdf) such that ncfcdf(uncorrected d', δ) equals 0.5 (i.e., the median), and determining the corrected d' value based on the determined δ. This correction addresses both the finite-sample bias and the bias at no-signal, providing a more accurate and reliable estimate of the system's detectability performance. The correction of the d' will be discussed in more detail below, with reference to method 400 shown in FIG. 4.

At operation 116, the image processing system determines whether the corrected d' is greater than a predetermined threshold. In other words, at operation 116 the system assesses whether the imaging devices' performance meets the desired criteria for object detectability. If the corrected d' does not exceed the threshold, the system proceeds to operation 118, where the image processing system adjusts the imaging system parameters based on the corrected d'. This adjustment is made to improve the system's performance to achieve the desired level of detectability. In one embodiment, the system may modify exposure settings to increase or decrease the dose level, thereby affecting the d' value. In another embodiment, the system may adjust one or more imaging system parameters based on a known or modeled relationship between the one or more parameters and d'.

However, if at operation 116 the corrected d' is greater than the pre-determined threshold, the system proceeds to operation 120, where the image processing system stores the imaging system parameters that resulted in a corrected d' exceeding the predetermined threshold. Storing the parameters that satisfied the d' threshold ensures that the calibrated imaging settings may be applied in future imaging tasks. In one embodiment, the system may store the parameters in a configuration file or database. In another embodiment, the system may update a set of default parameters to reflect the optimized settings, thereby streamlining the setup process for subsequent imaging sessions.

In this way, method 100 systematically calibrates the imaging system to ensure that it operates at an desired level of performance, as quantified by the corrected detectability index d'. The method leverages statistical tools and a novel analytical correction to address biases and non-uniformities, resulting in a robust and reliable calibration process that can be applied to a wide range of imaging equipment and modalities.

Figure 2:
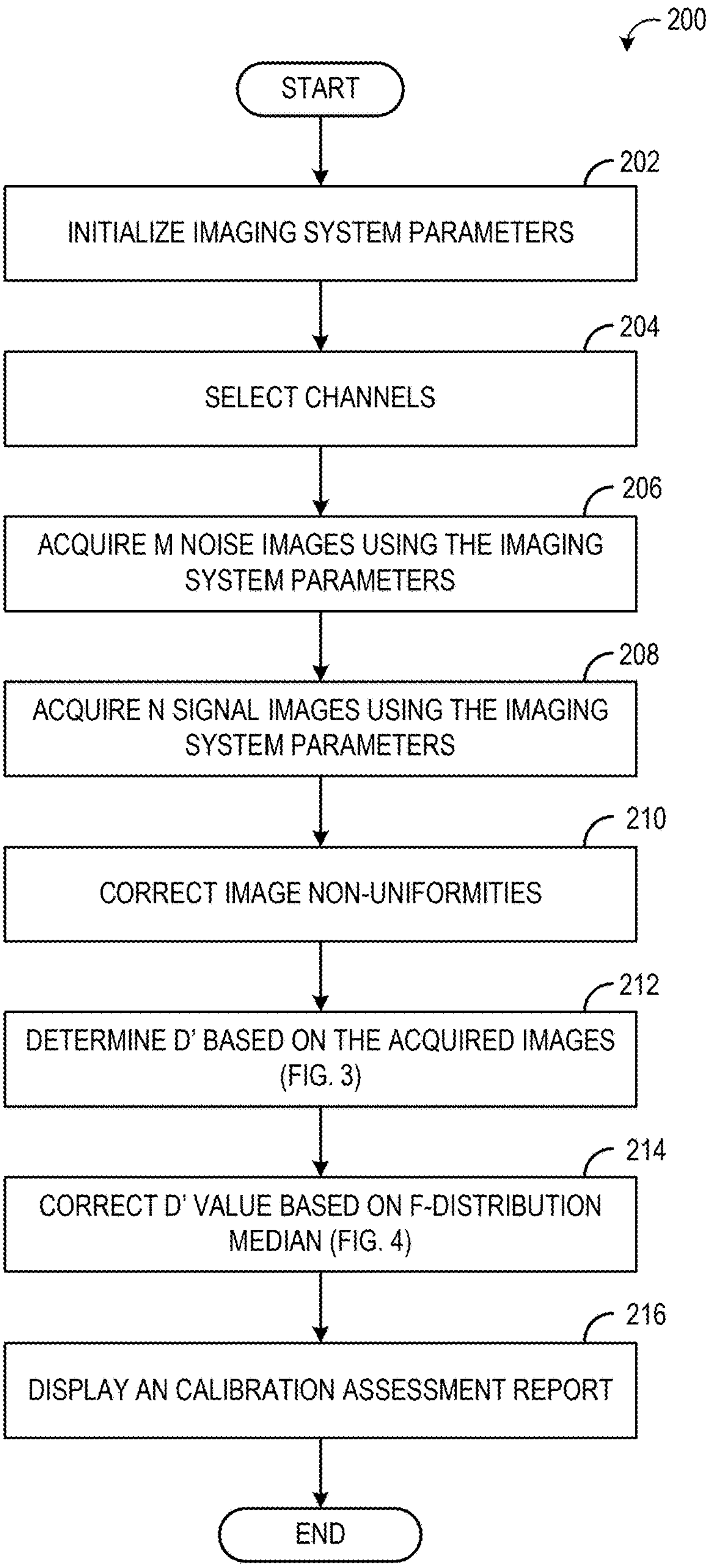
FIG. 2 is a flowchart illustrating a method for generating a calibration assessment report using the corrected d'.

Referring to FIG. 2, a method 200 for calibrating an imaging system and generating a calibration assessment report is disclosed. Method 200 employs a series of operations to optimize the imaging system's performance by utilizing a corrected detectability index (d'), indicative of the system's ability to discern objects within the acquired images. Method 200 is configured to ensure that imaging devices operate within desired performance specifications, which is enables accurate diagnostic images.

At operation 202, the image processing system initializes imaging system parameters. Operation 202 establishes baseline settings for subsequent image acquisition and analysis, which may facilitate the acquisition of high-quality images. The initialization includes setting parameters such as exposure levels, voltage, current, and other imaging conditions based on the particular imaging modalities employed or the diagnostic tasks being performed. The system initializes parameters based on predetermined protocols for particular diagnostic tasks or patient demographics, or to accommodate a range of imaging conditions, including Computed Tomography (CT), Magnetic Resonance Imaging (MRI), or X-ray systems.

At operation 204, the system selects channels based on the initialized imaging system parameters. Channels are selected for the extraction of relevant features from the image data and influence the performance of the Channelized Hotelling Observer (CHO) metric. The system may select channels such as Difference of Gaussians (DOG), dense DOG (DDOG), Gabor, Bandpass, or Laguerre-Gauss filters, based on the imaging task to be performed. Alternatively, the system may select channels based on the imaging system's characteristics or the specific diagnostic task for which the current calibration is being conducted.

At operation 206, the system acquires a plurality of noise images, denoted as M, using the initialized imaging system parameters. Noise images are captured without the presence of a signal and are used to characterize the noise properties of the imaging system. The number of noise images is selected to influence the accuracy of the noise characterization. The system may acquire noise images at different locations within the system's field of view to ensure comprehensive noise characterization. Alternatively, the system may acquire noise images under varying imaging conditions to account for potential variations in noise levels.

Following the acquisition of noise images, at operation 208, the system acquires a plurality of signal images, denoted as N, using the initialized imaging system parameters. Signal images are captured with the presence of a signal, such as a test object or a phantom, and are used to assess the system's ability to detect the signal amidst the noise. In some embodiments, signal images may be generated from the noise images acquired at operation 208 by incorporation of signal into the noise images via one or more analytical approaches known in the art. The number of signal images is selected to provide a representative sample for inferring the signal properties for the current imaging system parameters. The system may acquire signal images with varying signal strengths to evaluate the system's detectability performance across a range of conditions. Alternatively, the system may acquire signal images with different signal-to-noise ratios to simulate various clinical scenarios.

At operation 210, the system corrects image non-uniformities present in the acquired noise and signal images. Non-uniformities can introduce biases in the CHO metric and may impact the reliability of the calibration process. The system may apply a flat-field correction to equalize pixel values across the images. Alternatively, the system may employ correction algorithms that account for spatial and temporal variations in the image data, such as correcting for level non-uniformities by rescaling the average of images to a given level or performing spatial non-uniformities corrections if images cannot be taken at the same location.

Operation 212 involves determining an uncorrected detectability index (d') for the imaging system based on the corrected plurality of noise images and the corrected plurality of signal images. The uncorrected d' quantifies the system's ability to distinguish between noise and signal. The system may compute d' using the resubstitution method, which involves training and testing the CHO on the same set of images. The determination of the uncorrected d' is further detailed in method 300 shown in FIG. 3.

At operation 214, the system corrects the d' value based on the median of an F-distribution. This correction addresses both the finite-sample bias and the bias at no-signal, providing a more accurate and reliable estimate of the system's detectability performance. The system may compute the median of the F-distribution using the noncentral F cumulative distribution function, which is applied to the uncorrected d' value. The correction of the d' is further detailed in method 400 shown in FIG. 4.

At operation 216, the image processing system displays a calibration assessment report based on the corrected d'. The calibration assessment report provides an evaluation of the imaging system's performance and may include visual indicators representing the corrected d' relative to a predetermined d' threshold for the imaging system. The calibration assessment report may include graphical bars, color-coded regions, or numerical values, and may provide interactive elements to allow a user to initiate recalibration or parameter adjustment directly from the report. The report may include recommendations for adjusting the imaging system parameters if the corrected d' does not satisfy the predetermined d' threshold, such as modifying exposure settings or altering image acquisition protocols.

Following operation 216, method 200 concludes. Method 200 systematically calibrates the imaging system to ensure optimal performance, as quantified by the corrected detectability index d'. The method employs statistical tools and an analytical correction to address biases and non-uniformities, resulting in a robust and reliable calibration process applicable to various imaging equipment and modalities.

Referring to FIG. 3, a method 300 for calculating an uncorrected detectability index, d', based on channelized signal and noise images is disclosed. The method 300 is utilized by an image processing system to determine the detectability index, which quantifies approximate human detectability of objects in images captured by the imaging system. Method 300 is implemented as part of an imaging device calibration process, such as at operations 112 and 212 of methods 100 and 200, respectively.

At operation 302, the image processing system channelizes noise images and signal images. Channelization includes the application of a set of filters, referred to herein as channels, to the image data. These channels are designed to extract specific features from the images that efficiently encode aspects of human detectability of objects captured by the images. The channels, denoted by U, can be a vector of P channels, where P represents the total number of channels employed in the channelization process. Each channel is applied to the image data to transform the original unchannelized image, g, into a channelized form. The transformation is mathematically represented by the equation $v=U^t g$, where $U^t$ is the transposed matrix of the channels and g is an unchannelized image of size a×b pixels, where a and b are positive integers greater than one. The scalar product of $U^t$ with g yields the channelized image v, which is a vector where each element corresponds to the output from one of the P channels. Therefore, the dimension of the resulting channelized image v is equal to the number of channels P. As an example, if the system utilizes 40 channels, for instance, the resulting channelized image v will be a vector containing 40 data points, each representing the response of the image data to one of the 40 channels. The selection of channels U is based on the imaging system's parameters and the specific diagnostic task, with options including but not limited to DOG, DDOG, Gabor, Bandpass, or Laguerre-Gauss filters. The chosen set of channels U influences the performance of the CHO metric, d'.

At operation 304, the image processing system determines the average channelized noise image, denoted as $\overline{v}_{noise}$, by computing v for each of the M noise images, and then averaging these channelized noise images. The average channelized noise image represents the system's inherent noise characteristics and provides a reference or baseline for comparison with images acquired with signal present. In some embodiments, the system may average channelized noise images acquired under consistent imaging conditions to ensure consistency and may apply statistical methods to account for variations in the noise images due to different acquisition parameters or environmental factors.

At operation 306, the image processing system determines the average channelized signal image, denoted as $\overline{v}_{signal}$, by computing v for each of the N signal images, and then averaging these channelized signal images. These images are captured with the presence of a signal, such as a test object or a phantom, and reflect the system's response to the signal.

At operation 308, the image processing system determines the overall average channelized image, denoted as $\overline{v}$, from the noise images and signal images by combining the information from both to produce a composite channelized image that captures the overall characteristics of the imaging system's response. In some embodiments, the system computes the average channelized image by averaging the channelized noise and signal images separately and then combining the averages, e.g., via a weighted sum.

At operation 310, the image processing system determines the difference between the average channelized signal image, $\overline{v}_{signal}$, and the average channelized noise image, $\overline{v}_{noise}$, denoted as $\Delta\overline{v}$, which represents the signal detectability against the background noise. Expressed mathematically, $\Delta\overline{v}=\overline{v}_{signal}-\overline{v}_{noise}$.

At operation 312, the image processing system determines the covariance matrix of the channelized images, denoted as K. This matrix is created from the convolution of the vector $v-\overline{v}$ with itself (i.e., the outer product between the $i^{th}$ channelized image and the average of all channelized images) and averaged over all images, which includes both the signal present set and signal absent set. Expressed mathematically, the covariance matrix K is given by $$K=\sum_{i=1}^{M+N}\frac{(v_i-\overline{v})\otimes(v_i-\overline{v})}{M+N-2},$$

where ⊗ indicates an outer product between the matrix $(v_i-\overline{v})$ and itself. The covariance matrix K is a P×P matrix, where P is the number of channels, and is used for understanding the variability and correlation between different channelized images.

At operation 314, the image processing system determines the inverse of the covariance matrix, denoted as $K^{-1}$. In some embodiments, the system may use numerical methods to compute the inverse of the covariance matrix accurately and may employ matrix decomposition techniques to facilitate the inversion process, especially for large or ill-conditioned matrices.

At operation 316, the image processing system calculates the detectability index, d', using the resubstitution equation based on the inverse covariance matrix, and the difference between the average channelized signal image and the average channelized noise image, according to the equation $d'^2=\Delta\overline{v}^t K^{-1}\Delta\overline{v}$. The d' value obtained is an uncorrected measure of the system's detectability performance and serves as a basis for further corrections and optimizations. Thus, method 300 enables the calculation of the uncorrected d' value, which may then be corrected using one or more operations of method 400, described subsequently.

Referring to FIG. 4, a flowchart of a method 400 for determining a corrected d' value in an imaging system is shown. The method 400 is employed by an image processing system to enhance the accuracy of image quality assessments, thereby facilitating improved diagnostic capabilities in medical imaging applications. The method 400 leverages statistical tools and a novel analytical correction to address biases and non-uniformities, resulting in a robust and reliable calibration process that can be applied to a wide range of imaging equipment and modalities.

At operation 402, the image processing system sets parameters of a noncentral F cumulative distribution (ncfcdf) based on the number of acquired noise images, the number of acquired signal images, the number of channels, and the uncorrected d'. The noncentral F distribution is the ratio of two chi-square distributions with degrees of freedom ν1 and ν2, respectively, where each chi-square has first been divided by its degrees of freedom. The upper chi-square distribution has a non-central parameter delta while the lower chi-square distribution has a non-central parameter equal to zero. The cumulated distribution for a given probability distribution is the integral of the probability density function from minus infinity up to the given probability value In one embodiment, the ncfcdf may be expressed as:

$$ncfcdf(x \mid \nu_1, \nu_2, \delta) = \sum_{j=0}^{\infty}\left(\left(\frac{\left(\frac{1}{2}\delta\right)^j}{j!}e^{-\frac{\delta}{2}}\right)I\left(\frac{\nu_1 \cdot x}{\nu_2 + \nu_1 \cdot x} \,\middle|\, \frac{\nu_1}{2} + j, \frac{\nu_2}{2}\right)\right)$$

Where I(x|a, b) is the incomplete beta function with parameters a and b, $\nu_1=P$, $\nu_2=M+N-P-1$, δ is the noncentrality parameter (to be determined), and $$x = d'_{uncorrected}\frac{2(M+N-P-1)(MN)}{P(M+N-2)(M+N)},$$

where M+N>P+3, and where M is the number of noise images, N is the number of signal images, P is the number of channels, and $d_{uncorrected}'$ is the uncorrected detectability index as may be determined according to the operations of method 300. In one embodiment, the system may utilize a predetermined number of noise and signal images, such as 50, 100, 200, 400, 800, 1200, or 20000. In some embodiments, at operation 402 the image processing system may set an initial estimate of δ, which may be iteratively refined at 404.

At operation 404, the image processing system iteratively determines a value of delta (δ) which causes the noncentral F cumulative distribution with the given parameters to equal 0.5. In other words, at operation 404 the system determines a value for δ which causes $ncfcdf(x|\nu_1,\nu_2,\delta)=0.5$ for the values of x, $\nu_1$, and $\nu_2$ as set at operation 402. This operation identifies the noncentrality parameter, delta, that aligns the cumulative distribution function with the median value of 0.5. In one embodiment, the system may employ iterative numerical methods, such as the Newton-Raphson method or other root-finding algorithms, to accurately determine the delta value. The iterative process continues until the noncentral F cumulative distribution function, evaluated at the uncorrected d' value and with the determined delta, equals the target value of 0.5, which represents the median of the distribution. In some embodiments the system may rearrange the above equation as $ncfcdf(x|\nu_1,\nu_2,\delta)-0.5=0$ to conform with the expected format for input into a root finding algorithm.

In an alternative embodiment, the system may utilize a lookup table or precomputed values to expedite the determination of delta. This approach may be particularly advantageous in clinical environments where time efficiency is of particular relevance. The lookup table may be generated based on a range of typical values for the number of images, the number of channels, and the uncorrected d' values encountered in medical imaging applications. By referencing the table, the system can quickly approximate the delta value without the need for extensive iterative calculations.

At operation 406, the image processing system determines the corrected d' value based on delta (δ). In one embodiment the corrected d' may be determined based on the following equation:

$$d'_{corrected} = \sqrt{\delta\frac{M+N}{MN}}$$

Where δ is the noncentrality parameter (determined at operation 404), M is the number of noise images, N is the number of signal images, and $d_{corrected}'$ is the corrected detectability index. By employing an analytical correction based on the median of the noncentral F cumulative distribution function, the method 400 addresses biases and non-uniformities in a robust and reliable manner. The disclosed approach is computationally efficient and can be rapidly computed without processing a large number of images, enabling faster and more accurate calibration of imaging system devices. Consequently, the method 400 facilitates improved performance and potentially enhances diagnostic capabilities in medical imaging applications.

Referring to FIG. 5, an image processing system 500 for determining and correcting an image detectability index, d', is shown in accordance with an exemplary embodiment. The image processing system 500 is configured to enhance the calibration of imaging devices by employing an analytical correction of biases in CHO metrics. This system is particularly advantageous for medical imaging applications where precise and reliable image quality assessment enables accurate diagnostics.

The image processing system 500 comprises an image processing device 502, which includes a processor 504 and a non-transitory memory 506. The processor 504 is configured to execute machine-readable instructions stored in the non-transitory memory 506, which may include a d' determination module 508, a d' correction module 510, and image data 512. The system 500 further includes a user input device 550 and a display device 530, which facilitate user interaction with the system and visualization of the image data and computed d' values. Additionally, an imaging device 540 is communicably coupled to the image processing device 502, enabling the acquisition of noise and signal images used in the d' determination and correction process.

The non-transitory memory 506 of the image processing device 502 stores machine-readable instructions that, when executed by the processor 504, enable the system to perform one or more operations of the methods disclosed herein. The memory 506 stores the d' determination module 508, which is responsible for acquiring and processing a plurality of noise and signal images to determine an uncorrected detectability index (d'). The d' determination module 508 utilizes image data 512, which may include medical images captured by the imaging device 540, to compute the uncorrected d' based on the corrected plurality of noise images, the corrected plurality of signal images, and selected channels.

The d' correction module 510 within the non-transitory memory 506 applies an analytical correction to the uncorrected d' value. This correction is based on the median of an F-distribution, addressing both finite-sample bias and residual no-signal bias. The corrected d' is then compared to a predetermined threshold, and the imaging system parameters are adjusted accordingly to optimize the imaging device's performance. The d' correction module 510 employs a novel approach that is distinct from conventional methods, which typically address only one type of bias and often rely on statistical estimation of correction factors.

The user input device 550 may comprise a touchscreen, keyboard, mouse, or other input mechanisms, enabling a user to interact with the image processing system 500. Through the user input device 550, a user can initiate calibration processes, select images for processing, and adjust system parameters based on the calibration assessment report generated by the system.

The display device 530, which may include a monitor or touchscreen, is used to display the image data, the uncorrected and corrected d' values, and any visual indicators or calibration assessment reports. The display device 530 allows the user to visualize the effects of the corrections applied to the d' value and to make informed decisions regarding the calibration of the imaging system.

The imaging device 540, which may be an X-ray source, MRI, CT scanner, or other medical imaging equipment, is an integral component of the image processing system 500. The imaging device 540 is configured to acquire the noise and signal images that are used in the d' determination and correction process. The imaging device 540 is communicably coupled to the image processing device 502.

In one embodiment, the image processing system 500 may be utilized in a medical imaging facility where the calibration of imaging devices is employed for patient diagnosis and treatment planning. The system 500 can be applied to various imaging modalities, including but not limited to CT, MR imaging, Mammography, Interventional X-ray, and Ultrasound. In some embodiments, the image processing system 500 may be used in quality control (QC) testing of imaging devices, ensuring that they operate within the desired performance specifications.

In another embodiment, the image processing system 500 may include interactive elements that allow a user to initiate recalibration or parameter adjustment directly from the calibration assessment report displayed on the display device 530. This feature streamlines the calibration process, enabling rapid and efficient optimization of the imaging system's parameters.

Referring now to FIG. 6, depicted therein is a graph 600 that illustrates the relationship between various detectability index (d') values in the context of imaging system calibration. The graph 600 provides a visual depiction of the relationships between uncorrected d' values 602, conventionally zero-signal corrected d' values 608, and the corrected d' values proposed in the current disclosure, denoted as F-median (confidence interval 50%) 610. The graph 600 includes a confidence interval minimum 604 and a confidence interval maximum 606, which show a pre-determined range of confidence for the uncorrected d' 602.

The uncorrected d' values 602, as plotted on graph 600, represent the initial detectability index values determined by the imaging system without bias correction. These values are derived from the channelized images acquired using the imaging system parameters, as discussed in more detail in the description of method 300.

The conventionally zero-signal corrected d' values 608 are obtained by applying a known correction method to the uncorrected d' values 602. This conventional correction method adjusts for the zero-signal residual observed in the uncorrected d' 602, which can lead to inaccuracies in the d' estimation in conditions with low signal. The zero-signal corrected d' values 608 implement a quadratic correction to approximate the true detectability index near zero signal. The quadratic correction approach, while effective in addressing the zero-signal bias, introduces a level of computational inaccuracy and inefficiency that may not be ideal for real-time or high-throughput imaging scenarios. The process of applying the quadratic correction involves additional computational steps, such as the estimation of the zero-signal residual for d' and quadratic subtraction of the zero-signal residual from the uncorrected d' values. The determination of the zero-signal residual introduces statistical variations in the corrected d' values, since it is computed from a finite number of images.

The graph 600 also presents the confidence interval minimum 604 and confidence interval maximum 606, which define the range within which the true d' value is expected to lie with a certain level of confidence. The confidence interval minimum 604 represents the lower bound of the interval, while the confidence interval maximum 606 signifies the upper bound. The interval between 604 and 606 indicates the uncertainty associated with the d' estimation.

The corrected d' value, represented by the F-median (confidence interval 50%) 610 on the graph 600, is based on an analytical correction that utilizes the median of the F-distribution, derived from the noncentral F cumulative distribution function. The F-median 610 is computed based on a corresponding uncorrected d' 602, as discussed in more detail with reference to FIG. 4. The graph 600 shows that at lower values of uncorrected d' 602, the F-median 610 closely aligns with the quadratic no-signal correction 608, indicating the effectiveness of the proposed method in refining the d' estimation. The F-median 610 of the uncorrected d' 602 provides an accurate and reliable measure of the imaging system's performance, which is computationally cheaper to compute than the quadratic no-signal correction 608.

Referring now to FIG. 7, a graphical representation 700 is provided to illustrate the relationship between the zero-signal residual and the uncorrected d' which maps to a corrected d' value of zero, under various experimental conditions. The graph 700 presents the zero-signal residual on the horizontal axis, X-axis, and the uncorrected d' input that yields a zero value for the corresponding corrected d' on the vertical axis, Y-axis, when utilizing the disclosed noncentral F cumulative distribution function based d' correction.

The zero-signal residual, as depicted on the X-axis, represents the d' value obtained when no signal is present in the images being analyzed. This residual is an artifact of the statistical computation of d' and is expected to approach zero in an ideal scenario. However, due to inherent biases in the estimation process, a non-zero residual may be observed.

Graph 700 displays a linear relationship, with slope approximately equal to 1.0, between the zero-signal residual and the uncorrected d' input that corresponds to a corrected d' of zero. This linear fit is indicative of the efficacy of the disclosed correction at negating the zero-signal bias across a spectrum of conditions, including variations in the number of channels used for image analysis and the number of images comprising the signal and noise datasets. The conditions under which the uncorrected d' inputs were computed include a range of channel types, such as DOG, DDOG, Gabor channels, and others, as well as different combinations of signal and noise image counts.

The data points plotted on graph 700 are derived from multiple experimental setups, each characterized by a specific configuration of channels and image counts. The alignment of these data points along the linear fit line indicates the robustness of the proposed d' correction method. It confirms that the correction method consistently drives the zero-signal residual towards zero, regardless of the experimental setup, including variations in the number of images and the number or types of channels.

Graph 700 serves as a visual confirmation of the accuracy and consistency of the disclosed noncentral F cumulative distribution function based d' correction method. It provides a quantifiable demonstration that the method effectively neutralizes the zero-signal residual across diverse experimental conditions, thereby enhancing the reliability of the d' metric as a tool for calibrating the performance of imaging systems.

Referring now to FIG. 8, a graph 800 is depicted, which illustrates the relationship between the inverse of the number of images utilized in the computation of the detectability index, denoted as d', and the resulting values of d'. The graph 800 highlights the impact of image quantity on the precision of the detectability index within the context of imaging system device calibration, and demonstrates the efficacy of the herein proposed F-median based d' correction.

The X-axis of graph 800 is scaled to represent 1/(number of images), serving as a proxy for the sample size used in the computation of d'. The Y-axis corresponds to the computed values of d', a metric indicative of the signal-to-noise ratio and a surrogate for visual detectability performance. The graph 800 presents three distinct data trends, each corresponding to a different method of d' computation and correction for statistical biases inherent in the estimation process.

The first data trend, represented by the uncorrected d' curve 802, is characterized by a series of data points that exhibit a linear relationship, as evidenced by the linear fit to uncorrected d' 808. This trend line demonstrates an inverse correlation between the number of images and the d' values, indicating that as the number of images decreases, the d' values increase. This phenomenon is attributable to the finite-sample bias, a statistical artifact that arises when the sample size is limited, leading to an overestimation of the detectability index.

The second data trend, depicted by the gamma corrected d' curve 804, introduces a multiplicative bias correction factor, gamma, into the computation of d'. The gamma correction is computed as gamma=(M+N−P−3)/(M+N−2), where M is the number of noise images, N is the number of noise+signal images, and P is the number of channels. The application of this gamma correction yields a modified set of d' values, which are plotted and fitted with a linear fit to gamma corrected d' 810. The gamma correction mitigates the influence of finite-sample bias, and while it does not eliminate the dependence of d' on the number of images, it results in an attenuation of this relationship. The slope of the linear fit to gamma corrected d' 810 is less steep compared to the uncorrected counterpart, suggesting a reduction in the bias effect caused by the finite number of samples.

The third data trend is represented by the F-median corrected d' curve 806. This curve represents d' values that have been adjusted using the median of the F-distribution, as discussed herein. The linear fit to F-median corrected d' 812, derived from these adjusted d' values, exhibits a flatter slope, indicating a diminution in the dependence of d' on the number of images. This trend is indicative of an effective correction of the finite-sample bias, resulting in d' values that are less influenced by the sample size and thus more reliable for device optimization purposes across a range of sample sizes.

Referring now to FIG. 9, a graph 900 is depicted, which illustrates the relationship between the inverse of the number of images utilized in the computation of the detectability index, denoted as d', and the resulting values of d'. The graph 900 highlights the impact of image quantity on the precision of the detectability index within the context of imaging system device calibration, and demonstrates the efficacy of the herein proposed F-median based d' correction.

The X-axis of graph 900 is scaled to represent 1/(number of images), representing the inverse of the sample size used in the computation of d'. The Y-axis corresponds to the computed values of d', a metric indicative of the signal-to-noise ratio and a surrogate for visual detectability performance. The graph 900 presents several distinct data trends, each corresponding to a different method of d' computation and correction for statistical biases inherent in the estimation process.

The first data trend, represented by the uncorrected d' curve 902, is characterized by a series of data points that exhibit a linear relationship, as evidenced by the linear fit to uncorrected d' 902. This trend line demonstrates an inverse correlation between the number of images and the d' values, indicating that as the number of images decreases, the d' values increase. This phenomenon is attributable to the finite-sample bias, a statistical artifact that arises when the sample size is limited, leading to an overestimation of the detectability index.

The second data trend, depicted by the F-median corrected d' curve 904, represents d' values that have been adjusted using the median of the F-distribution, as discussed herein. The linear fit to F-median corrected d' 904, derived from these adjusted d' values, exhibits a flatter slope, indicating a diminution in the dependence of d' on the number of images. This trend is indicative of an effective correction of the finite-sample bias, resulting in d' values that are less influenced by the sample size and thus more reliable for device optimization purposes across a range of sample sizes.

The third data trend, represented by the linear corrected d' curve 906, shows a decrease in d' as the number of images used to determine d' decreases. This trend suggests that the linear correction method over compensates for the finite-sample bias, resulting different, but still undesirable dependence of d' on the sample size.

The fourth and fifth data trends, represented by the first quadratic corrected d' curve 908 and the second quadratic corrected d' curve 910, respectively, show attenuated increases in d' as the number of images used to determine d' decreases. These curves suggest that the quadratic correction methods provide a reduction in the finite-sample bias compared to the uncorrected d' values. However, the first quadratic corrected d' 908 and the second quadratic corrected d' 910 still exhibit a substantial dependence of d' on the number of images, with the second quadratic corrected d' 910 showing a larger dependence than the first quadratic corrected d' 908.

Turning now to FIGS. 10, 11, and 12, depicted therein are graphical representations, namely graphs 1000, 1100, and 1200, respectively. Each graph presents a quantitative analysis of the detectability index, denoted as d', in relation to signal amplitude across a spectrum of conditions. The X-axis of each graph represents the signal amplitude, while the Y-axis corresponds to the computed values of d'. These graphs illustrate the performance of various correction methods applied to mitigate the zero-signal residual, also known as the bias at no-signal, which is a factor in the calibration of imaging systems.

Graph 1000, as shown in FIG. 10, provides a baseline representation where d' is uncorrected. This graph includes data for five distinct signal image sample sizes, specifically 100, 200, 300, 400, and 500. Each sample size is plotted against a plurality of different signal amplitudes, providing a view of the system's performance without the application of bias correction. Graph 1000 reveals a zero-signal residual, indicative of the inherent bias present when no correction is applied. Additionally, there is a deviation from the expected linear dependence of d' on signal amplitude, particularly near the zero value of the signal amplitude.

Graph 1100, as illustrated in FIG. 11, demonstrates the application of a gamma correction to d'. Similar to graph 1000, graph 1100 includes five different signal image sample sizes, each plotted at various signal amplitudes. Despite the application of the gamma correction, graph 1100 exhibits a zero-signal residual. While the gamma correction may partially address the bias at no-signal, its effectiveness is incomplete, as evidenced by the residual bias depicted in the graph 1100.

Graph 1200, presented in FIG. 12, showcases the application of an F-median correction to d', as taught herein. This graph also includes the same five signal image sample sizes as graphs 1000 and 1100, plotted against a range of signal amplitudes. In contrast to graphs 1000 and 1100, graph 1200 demonstrates a substantially complete reduction of the zero-signal residual. The F-median correction method, based on the median of the noncentral F cumulative distribution function, is effective in rectifying the bias at no-signal. The result is a linear relationship between the corrected d' and the signal amplitude, which is consistent across the entire range of signal amplitudes and sample sizes. The linearity and reduced residual bias in graph 1200 indicate an improvement in the accuracy of d' estimation, which is beneficial for the optimization and calibration of medical imaging devices.

The disclosure also provides support for a method for calibrating an imaging system, comprising: initializing imaging system parameters, selecting channels based on the initialized imaging system parameters, acquiring a plurality of noise images using the imaging system parameters, acquiring a plurality of signal images using the imaging system parameters, correcting non-uniformities present in the plurality of noise images and the plurality of signal images, determining an uncorrected detectability index (d') for the imaging system based on the corrected plurality of noise images, the corrected plurality of signal images, and the channels, correcting the uncorrected d' based on a median of an F-distribution of the uncorrected d' to obtain a corrected d', comparing the corrected d' to a predetermined threshold, and adjusting the imaging system parameters based on the comparison of the corrected d' to the predetermined threshold. In a first example of the method, correcting non-uniformities present in the plurality of noise images and the plurality of signal images includes applying a flat-field correction to equalize pixel values across the plurality of noise images and the plurality of signal images. In a second example of the method, optionally including the first example, acquiring the plurality of noise images and the plurality of signal images includes capturing images at different locations within a field of view of the imaging system. In a third example of the method, optionally including one or both of the first and second examples, correcting the uncorrected d' based on the median of the F-distribution includes determining a set of parameters of a noncentral F cumulative distribution function which causes the noncentral F cumulative distribution function to equal 0.5 for the uncorrected d', and determining the median of the F-distribution based on the set of parameters. In a fourth example of the method, optionally including one or more or each of the first through third examples, adjusting the imaging system parameters includes modifying exposure settings based on the comparison of the corrected d' to the predetermined threshold. In a fifth example of the method, optionally including one or more or each of the first through fourth examples, selecting channels based on the initialized imaging system parameters comprises selecting a channel type from a group consisting of Difference of Gaussians (DOG), dense DOG (DDOG), Gabor, Bandpass, and Laguerre-Gauss filters.

The disclosure also provides support for an imaging system, comprising: a memory storing instructions, an imaging device, and a processor communicably coupled to the memory and the imaging device, wherein the processor is configured to execute the instructions to: initialize imaging system parameters for the imaging device, select channels based on the initialized imaging system parameters, acquire a plurality of noise images and a plurality of signal images using the imaging system parameters, correct non-uniformities present in the acquired plurality of noise images and the plurality of signal images, determine an uncorrected detectability index (d') for the imaging system based on the corrected plurality of noise images, the corrected plurality of signal images, and the channels, correct the uncorrected d' based on a median of an F-distribution of the uncorrected d' to obtain a corrected d', compare the corrected d' to a predetermined threshold, and adjust the imaging system parameters based on the comparison of the corrected d' to the predetermined threshold. In a first example of the system, the processor is further configured to execute the instructions to apply a flat-field correction to the acquired plurality of noise images and the plurality of signal images to correct for spatial non-uniformities. In a second example of the system, optionally including the first example, the processor is configured to correct the uncorrected d' based on the median of the F-distribution of the uncorrected d' to obtain a corrected d' by: determining a set of parameters of the noncentral F cumulative distribution function which causes the noncentral F cumulative distribution function to equal 0.5 for the uncorrected d', and determining the median of the F-distribution based on the set of parameters. In a third example of the system, optionally including one or both of the first and second examples, the imaging device includes an X-ray source, and wherein the processor is further configured to execute the instructions to modulate an X-ray dose based on the comparison of the corrected d' to the predetermined threshold.

The disclosure also provides support for a method for calibrating parameters of an imaging system, comprising: initializing imaging system parameters, acquiring a plurality of noise images using the initialized imaging system parameters, acquiring a plurality of signal images using the initialized imaging system parameters, correcting image non-uniformities present in the plurality of noise images and the plurality of signal images, selecting a plurality of channels, channelizing the plurality of noise images and the plurality of signal images using the plurality of channels to produce a plurality of channelized noise images and a plurality of channelized signal images, determining an uncorrected detectability index (d') based on the plurality of channelized noise images and the plurality of channelized signal images, correcting the uncorrected d' based on a median of an F-distribution of the uncorrected d' to obtain a corrected d', and displaying a calibration assessment report based on the corrected d'. In a first example of the method, selecting channels comprises choosing channels based on a type of imaging examination to be performed. In a second example of the method, optionally including the first example, an imaging modality of the plurality of noise images and the plurality of signal images is one of Computed Tomography (CT), Magnetic Resonance (MR) image, Mammography, X-ray, Radiography and Fluoroscopy (R/F), Dental imaging, Ultrasound, Industrial Radiography, Positron Emission Tomography (PET), and Optical imaging. In a third example of the method, optionally including one or both of the first and second examples, correcting image non-uniformities comprises at least one of level non-uniformities correction and spatial non-uniformities correction. In a fourth example of the method, optionally including one or more or each of the first through third examples, a sum of the plurality of noise images and the plurality of signal images is at least three greater than a number of the plurality of channels. In a fifth example of the method, optionally including one or more or each of the first through fourth examples, the calibration assessment report comprises a comparison between the corrected d' and a predetermined d' threshold, the comparison indicating whether the imaging system parameters are within a pre-determined range for a selected imaging task. In a sixth example of the method, optionally including one or more or each of the first through fifth examples, the calibration assessment report further comprises recommendations for adjusting the imaging system parameters if the corrected d' does not satisfy the predetermined d' threshold. In a seventh example of the method, optionally including one or more or each of the first through sixth examples, the recommendations for adjusting the imaging system parameters include at least one of modifying exposure settings, or altering image acquisition protocols. In a eighth example of the method, optionally including one or more or each of the first through seventh examples, the calibration assessment report is displayed via a user display device, the calibration assessment report including visual indicators representing the corrected d' relative to an predetermined d' threshold for the imaging system. In a ninth example of the method, optionally including one or more or each of the first through eighth examples, the visual indicators comprise at least one of graphical bars, color-coded regions, or numerical values, and wherein the user display device provides interactive elements to allow a user to initiate recalibration or parameter adjustment directly from the calibration assessment report.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for calibrating an imaging system, comprising:

initializing imaging system parameters;

selecting channels based on the initialized imaging system parameters;

acquiring a plurality of noise images using the imaging system parameters;

acquiring a plurality of signal images using the imaging system parameters;

correcting non-uniformities present in the plurality of noise images and the plurality of signal images;

determining an uncorrected detectability index (d') for the imaging system based on the corrected plurality of noise images, the corrected plurality of signal images, and the channels;

correcting the uncorrected d' based on a median of an F-distribution of the uncorrected d' to obtain a corrected d';

comparing the corrected d' to a predetermined threshold; and adjusting the imaging system parameters based on the comparison of the corrected d' to the predetermined threshold.

2. The method of claim 1, wherein correcting non-uniformities present in the plurality of noise images and the plurality of signal images includes applying a flat-field correction to equalize pixel values across the plurality of noise images and the plurality of signal images.

3. The method of claim 1, wherein acquiring the plurality of noise images and the plurality of signal images includes capturing images at different locations within a field of view of the imaging system.

4. The method of claim 1, wherein correcting the uncorrected d' based on the median of the F-distribution includes determining a set of parameters of a noncentral F cumulative distribution function which causes the noncentral F cumulative distribution function to equal 0.5 for the uncorrected d', and determining the median of the F-distribution based on the set of parameters.

5. The method of claim 1, wherein adjusting the imaging system parameters includes modifying exposure settings based on the comparison of the corrected d' to the predetermined threshold.

6. The method of claim 1, wherein selecting channels based on the initialized imaging system parameters comprises selecting a channel type from a group consisting of Difference of Gaussians (DOG), dense DOG (DDOG), Gabor, Bandpass, and Laguerre-Gauss filters.

7. An imaging system, comprising:

a memory storing instructions;

an imaging device; and a processor communicably coupled to the memory and the imaging device, wherein the processor is configured to execute the instructions to:

initialize imaging system parameters for the imaging device;

select channels based on the initialized imaging system parameters;

acquire a plurality of noise images and a plurality of signal images using the imaging system parameters;

correct non-uniformities present in the acquired plurality of noise images and the plurality of signal images;

determine an uncorrected detectability index (d') for the imaging system based on the corrected plurality of noise images, the corrected plurality of signal images, and the channels;

correct the uncorrected d' based on a median of an F-distribution of the uncorrected d' to obtain a corrected d';

compare the corrected d' to a predetermined threshold; and adjust the imaging system parameters based on the comparison of the corrected d' to the predetermined threshold.

8. The imaging system of claim 7, wherein the processor is further configured to execute the instructions to apply a flat-field correction to the acquired plurality of noise images and the plurality of signal images to correct for spatial non-uniformities.

9. The imaging system of claim 7, wherein the processor is configured to correct the uncorrected d' based on the median of the F-distribution of the uncorrected d' to obtain the corrected d' by:

determining a set of parameters of a noncentral F cumulative distribution function which causes the noncentral F cumulative distribution function to equal 0.5 for the uncorrected d'; and determining the median of the F-distribution based on the set of parameters.

10. The imaging system of claim 7, wherein the imaging device includes an X-ray source, and wherein the processor is further configured to execute the instructions to modulate an X-ray dose based on the comparison of the corrected d' to the predetermined threshold.

11. A method for calibrating parameters of an imaging system, comprising:

initializing imaging system parameters;

acquiring a plurality of noise images using the initialized imaging system parameters;

acquiring a plurality of signal images using the initialized imaging system parameters;

correcting image non-uniformities present in the plurality of noise images and the plurality of signal images;

selecting a plurality of channels;

channelizing the plurality of noise images and the plurality of signal images using the plurality of channels to produce a plurality of channelized noise images and a plurality of channelized signal images;

determining an uncorrected detectability index (d') based on the plurality of channelized noise images and the plurality of channelized signal images;

correcting the uncorrected d' based on a median of an F-distribution of the uncorrected d' to obtain a corrected d'; and displaying a calibration assessment report based on the corrected d'.

12. The method of claim 11, wherein selecting channels comprises choosing channels based on a type of imaging examination to be performed.

13. The method of claim 11, wherein an imaging modality of the plurality of noise images and the plurality of signal images is one of Computed Tomography (CT), Magnetic Resonance (MR) image, Mammography, X-ray, Radiography and Fluoroscopy (R/F), Dental imaging, Ultrasound, Industrial Radiography, Positron Emission Tomography (PET), and Optical imaging.

14. The method of claim 11, wherein correcting image non-uniformities comprises at least one of level non-uniformities correction and spatial non-uniformities correction.

15. The method of claim 11, wherein a sum of the plurality of noise images and the plurality of signal images is at least three greater than a number of the plurality of channels.

16. The method of claim 11, wherein the calibration assessment report comprises a comparison between the corrected d' and a predetermined d' threshold, the comparison indicating whether the imaging system parameters are within a pre-determined range for a selected imaging task.

17. The method of claim 16, wherein the calibration assessment report further comprises recommendations for adjusting the imaging system parameters if the corrected d' does not satisfy the predetermined d' threshold.

18. The method of claim 17, wherein the recommendations for adjusting the imaging system parameters include at least one of modifying exposure settings, or altering image acquisition protocols.

19. The method of claim 11, wherein the calibration assessment report is displayed via a user display device, the calibration assessment report including visual indicators representing the corrected d' relative to an predetermined d' threshold for the imaging system.

20. The method of claim 19, wherein the visual indicators comprise at least one of graphical bars, color-coded regions, or numerical values, and wherein the user display device provides interactive elements to allow a user to initiate recalibration or parameter adjustment directly from the calibration assessment report.

* * * * *